(12) United States Patent
von Dyck et al.

(10) Patent No.: US 7,087,041 B2
(45) Date of Patent: Aug. 8, 2006

(54) PAD FOR USE WITH CONTINENT OSTOMY PORT

(75) Inventors: Peter M. von Dyck, Fernandina Beach, FL (US); James G. Schneider, Chesterfield, MO (US); Nick Martino, Fernandina Beach, FL (US); John S. Minasi, Amelia Island, FL (US); Tung Le, St. Louis, MO (US)

(73) Assignee: Zassi Medical Evolutions, Inc., Fernandina Beach, FL (US)

( * ) Notice: Subject to any disclaimer, the term of this patent is extended or adjusted under 35 U.S.C. 154(b) by 325 days.

(21) Appl. No.: 09/995,012

(22) Filed: Nov. 26, 2001

(65) Prior Publication Data

US 2002/0077611 A1 Jun. 20, 2002

Related U.S. Application Data

(60) Continuation-in-part of application No. 09/420,643, filed on Oct. 19, 1999, now Pat. No. 6,350,255, which is a division of application No. 09/030,685, filed on Feb. 25, 1998, now Pat. No. 6,033,390.

(51) Int. Cl.
*A61F 5/44* (2006.01)
(52) U.S. Cl. .................. 604/332; 604/336; 604/338
(58) Field of Classification Search ............ 128/893, 128/894; 602/41–59; 604/174, 332, 264, 604/179, 180, 336, 338, 344; 606/29, 31, 606/32
See application file for complete search history.

(56) References Cited

U.S. PATENT DOCUMENTS

| 2,054,535 A | 9/1936 | Diack |
| 2,327,514 A | 8/1943 | Fenwick |
| 2,457,244 A | 12/1948 | Lamson |

(Continued)

FOREIGN PATENT DOCUMENTS

DE 23 35 858 A1 1/1975

(Continued)

OTHER PUBLICATIONS

Thomas W. Duerig, Alan R. Pelton, and Kieter Stöckel; Superelastic Nitinol for Medical Devices; Mar./Apr. 1997.

*Primary Examiner*—Henry Bennett
*Assistant Examiner*—Kari Petrik
(74) *Attorney, Agent, or Firm*—Husch & Eppenberger, LLC; Rebecca J. Brandau

(57) ABSTRACT

A pad for use with a continent ostomy port includes a body portion having an internal wall defining an aperture appropriately sized to place around a stoma. The body portion is sized and shaped for placement against a user's skin beneath a face plate of an ostomy port and is formed of a material to cushion and protect the skin from contact with the face plate. The body portion has a stepped configuration of at least two distinct levels on a distal surface thereof, including a first level and a second level, the first level having a perimeter sized and shaped to fit within a perimeter of a face plate lip, and the second level extending parallel to the first level and having a perimeter extending beyond the perimeter of the first level, beneath the lip of the plate, to thereby protect the use's skin from friction irritation.

28 Claims, 23 Drawing Sheets

U.S. PATENT DOCUMENTS

| | | | |
|---|---|---|---|
| 2,510,766 A | 6/1950 | Surface | |
| 2,544,579 A | 3/1951 | Ardner | |
| 2,931,353 A | 4/1960 | Kitzul | |
| 3,301,254 A * | 1/1967 | Schickendanz | 128/894 |
| 3,447,533 A | 6/1969 | Spicer | |
| 3,606,886 A * | 9/1971 | Bittner | 128/894 |
| 3,802,418 A | 4/1974 | Clayton | |
| 3,830,235 A | 8/1974 | Marsan | |
| 4,019,499 A | 4/1977 | Fitzgerald | |
| 4,030,500 A | 6/1977 | Ronnquist | |
| 4,077,409 A | 3/1978 | Murray et al. | |
| 4,117,847 A | 10/1978 | Clayton | |
| 4,121,589 A | 10/1978 | McDonnell | |
| 4,137,918 A | 2/1979 | Bogert | |
| 4,209,009 A | 6/1980 | Hennig | |
| 4,210,131 A | 7/1980 | Perlin | |
| 4,219,023 A * | 8/1980 | Galindo | |
| 4,245,652 A | 1/1981 | Kelly et al. | |
| 4,258,704 A | 3/1981 | Hill | |
| 4,261,340 A | 4/1981 | Baumel et al. | |
| 4,306,563 A | 12/1981 | Iwatschenko | |
| 4,338,941 A | 7/1982 | Payton | |
| 4,344,434 A | 8/1982 | Robertson | |
| 4,381,765 A | 5/1983 | Burton | |
| 4,634,421 A | 1/1987 | Hegemann | |
| 4,662,890 A | 5/1987 | Burton | |
| 4,721,508 A | 1/1988 | Burton | |
| 4,786,283 A | 11/1988 | Andersson | |
| 4,804,375 A | 2/1989 | Robertson | |
| 4,867,748 A * | 9/1989 | Samuelsen | 604/336 |
| 4,943,276 A | 7/1990 | Ghedina | |
| 4,981,465 A | 1/1991 | Ballan et al. | |
| 5,030,199 A | 7/1991 | Barwick et al. | |
| 5,045,052 A | 9/1991 | Sans | |
| 5,208,313 A * | 5/1993 | Krishnan | 528/28 |
| 5,261,898 A | 11/1993 | Polin et al. | |
| 5,300,047 A | 4/1994 | Beurrier | |
| 5,569,216 A | 10/1996 | Kim | |
| 5,944,683 A * | 8/1999 | Baranowski | 602/65 |
| 6,350,255 B1 * | 2/2002 | von Dyck | 604/338 |

FOREIGN PATENT DOCUMENTS

| | | |
|---|---|---|
| DE | 27 54 207 | 3/1979 |
| EP | 0 188 376 A1 | 4/1986 |
| GB | 788407 | 1/1958 |
| GB | 1363644 | 8/1974 |
| GB | 2 153 686 A | 8/1985 |
| GB | 2 202 746 A | 10/1988 |
| SU | 1447-356 A | 12/1988 |

\* cited by examiner

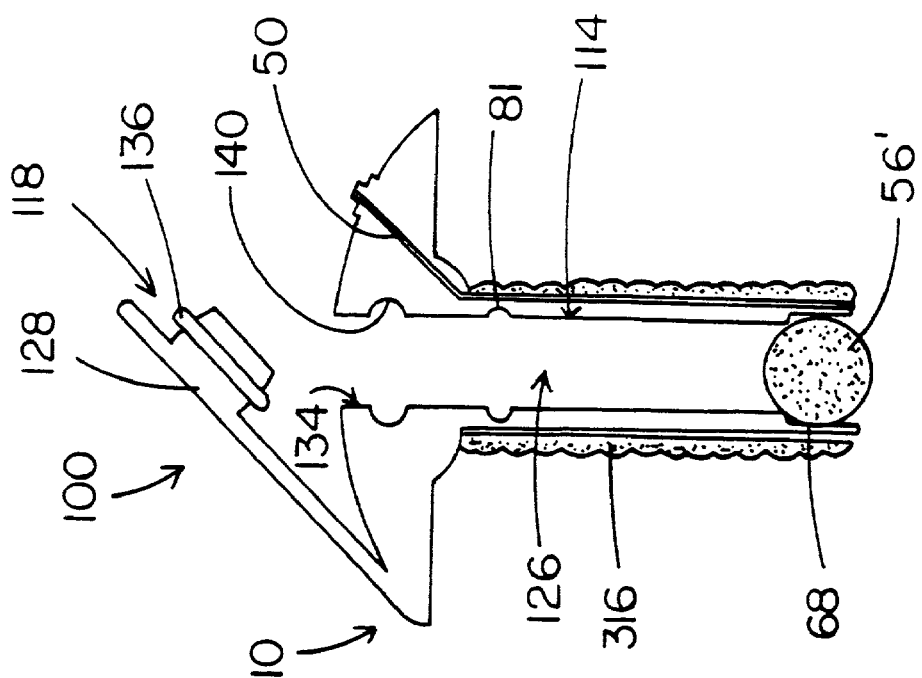
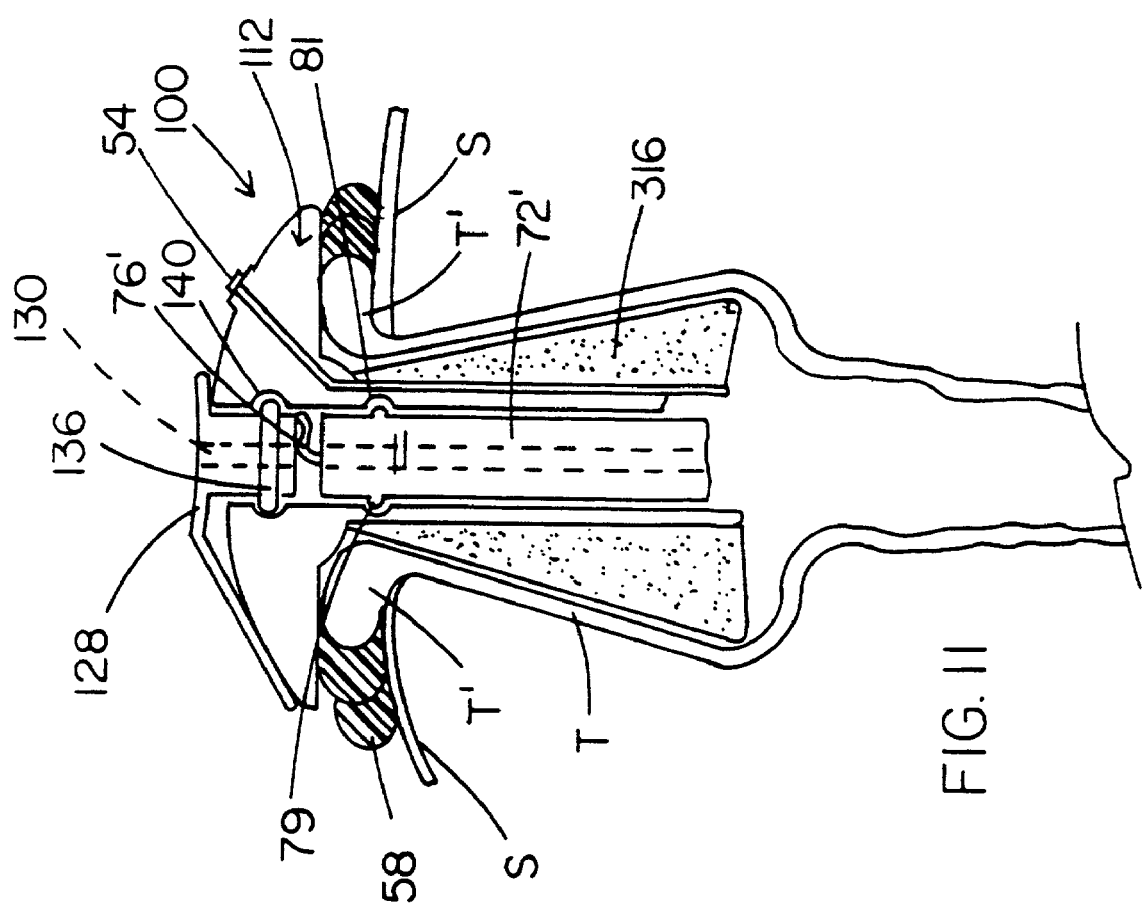
FIG. 12
FIG. 11

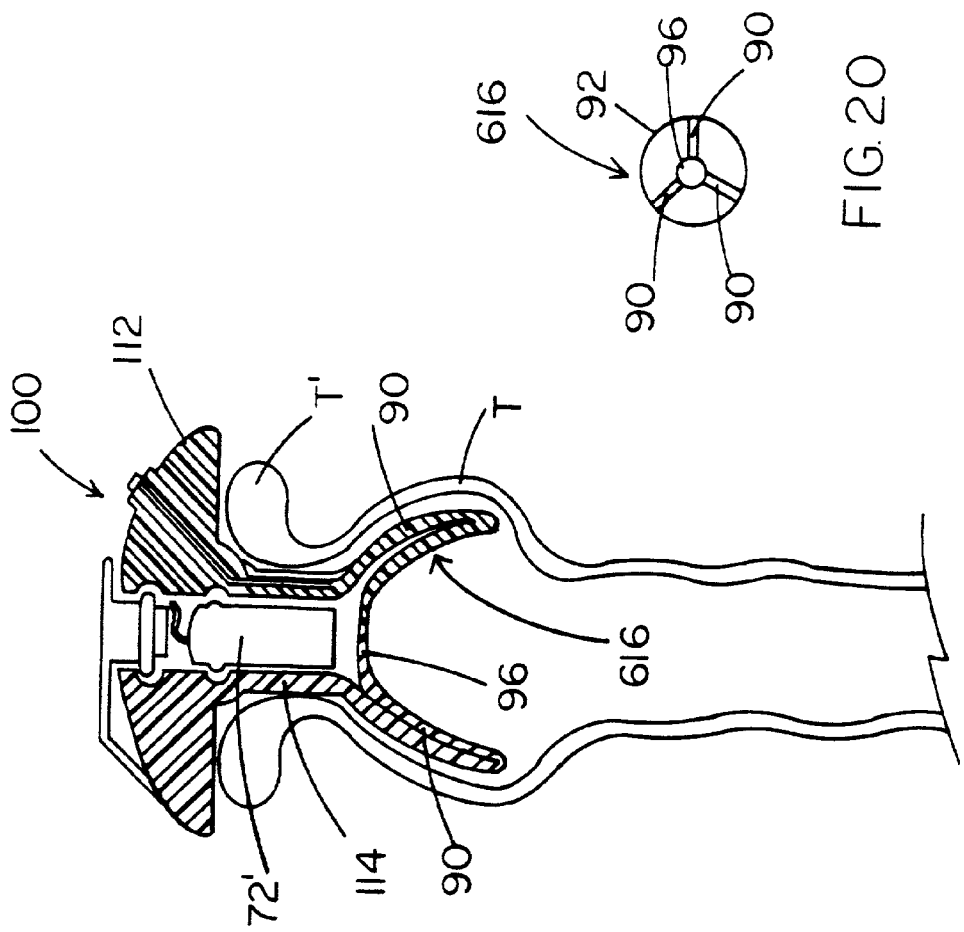
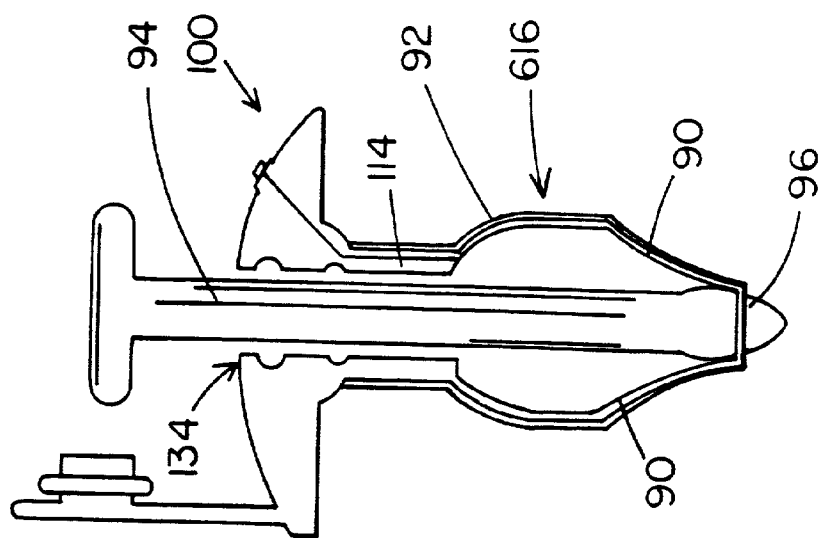

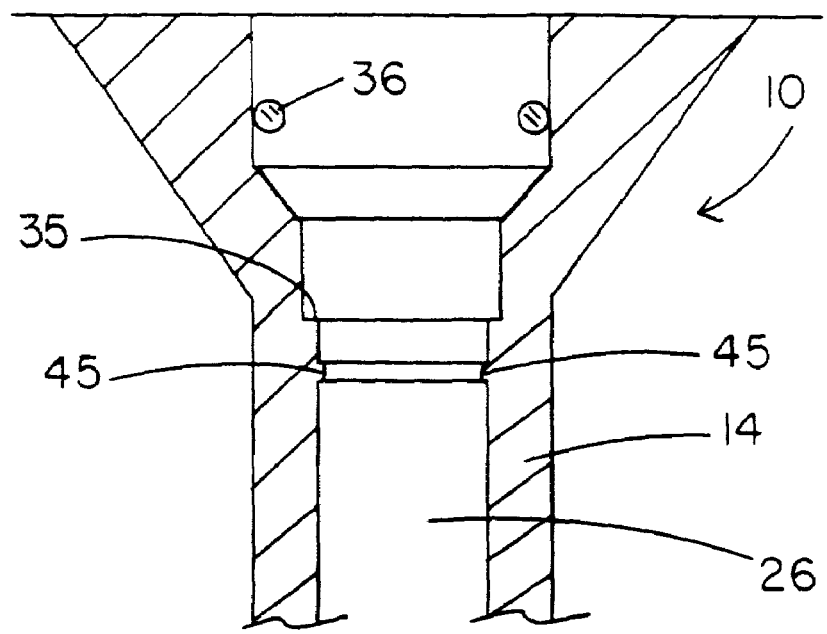
FIG. 24
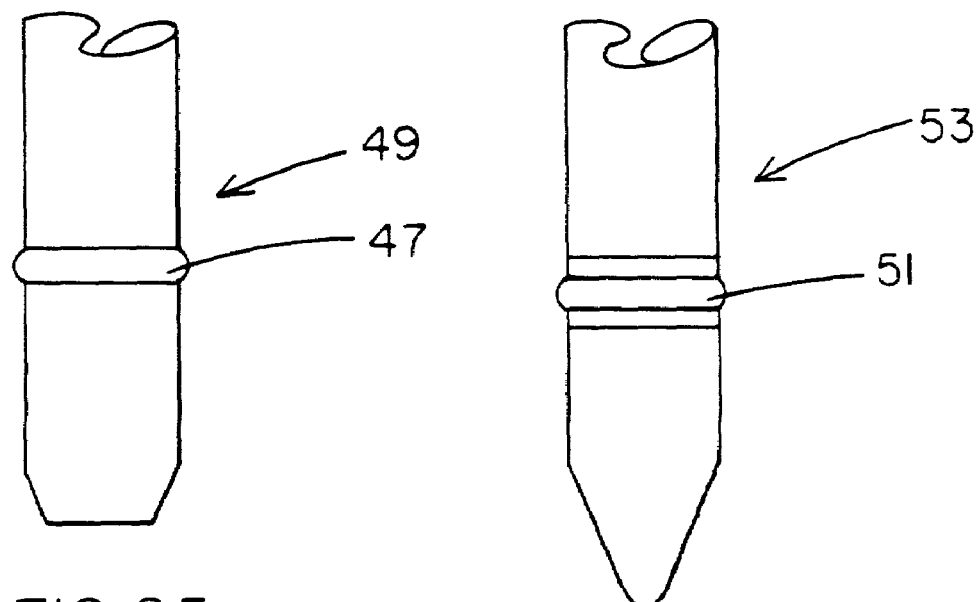
FIG. 25
FIG. 26

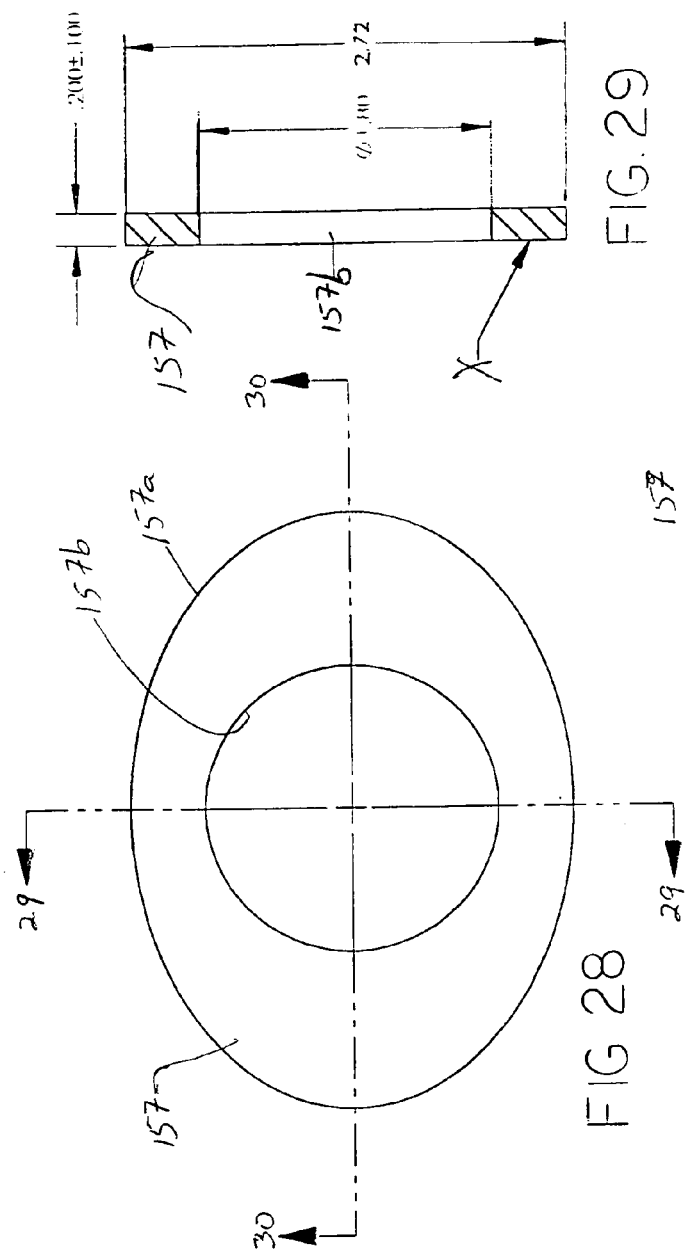

PAD FOR USE WITH CONTINENT OSTOMY PORT

RELATED APPLICATIONS

This application is a Continuation-In-Part application which claims the benefit of pending U.S. patent application Ser. No. 09/420,643, filed on Oct. 19, 1999 now U.S. Pat. No. 6,350,255, which is a Divisional of and which claims the benefit of U.S. patent application Ser. No. 09/030,685, filed Feb. 25, 1998, issued Mar. 7, 2000 as U.S. Pat. No. 6,033,390.

BACKGROUND AND SUMMARY OF THE INVENTION

1. Field of the Invention

The present invention relates to the field of ostomy devices, and, more particularly, to a self-retaining ostomy port which can be inserted into a stoma and secured for long-term placement without the use of adhesives, belts, bandages or revisionary surgical measures, and thus allows the user to be effectively "continent". The new ostomy port features a low profile and can be repeatedly selectively opened and closed without removal from the stoma, as may be necessary or desired by the individual user, and does not require the constant attachment of an ostomy bag or pouch.

2. Background of the Invention

Surgically formed stomas may be of a variety of types, including, but not limited to, ileostomies, colostomies and urostomies. Although the discussion below will usually describe the invention with reference to the stoma resulting from a colostomy procedure, it is to be understood that the new continent ostomy port can be applied to other types of stomas as well including those interfacing with internal reservoirs. Ostomates, individuals provided with a stoma, have historically been faced with a variety of problems not ordinarily experienced by the general (non-stoma bearing) public. These problems have included seepage of intestinal gas and waste, such as mucous and liquid and solid fecal material from around the site of the stoma. Such seepage not only causes unpleasant and embarrassing odors, but also leads to health problems, such as necrosis of the tissue surrounding the stoma site, creating the additional problems of increased expense and health risks related to further surgery to relocate or modify the existing stoma.

Traditional ostomies generally require the patient to have a bag or container of some sort attached to the ostomy for constant collection of body waste. Necessarily, the bag will become heavy and cumbersome as it automatically fills with body waste over time, and the user is faced with the risk of spillage from the bag, while in place, as well as during the process of emptying the bag's contents. Further, the material of the bag (as well as some adhesives) can cause allergic reactions in some users, and the bag material also makes bothersome noises during movement as the bag rubs against the user's clothing. For many ostomates, the bulk of the bag beneath clothing is also a problem. All these aspects of having an ostomy can deter social activities of all types, and especially any which are relatively more physical in nature. Frequently isolation and depression result.

The known art has made a variety of attempts to address these problems, without complete success. Although the majority of ostomates use bags to manage the ostomy excretions, a number of barrier devices have been developed which essentially plug or seal the stoma until the user is ready to purge, with resultant problems further discussed hereafter, which were not clinically viable, and in many cases, have necessitated revisionary surgery. By contrast, the new continent ostomy port is just that, a port, not a sealed closure or plug. Rather, constant but gradual, filtered, controlled venting of intestinal gas is provided with the new port, relieving the user from discomfort of internal pressure build-up, and also permitting quick and facile access for irrigation and purging the ostomy without removing the port from the stoma.

One such previous device included strong magnets in the external portion of the closure and magnets surgically sealed within the user's skin for transdermal connection of the ostomy plug-type closure. Leakage and skin irritation can result from use of such a device. Alternatively, if the plug is too tight, an extremely uncomfortable, even painful, build-up of intestinal gasses can occur. Known stoma closure or plugging systems also suffer, inter alia, from the problem of not being adjustable in response to daily variations in the user's body, as well as variations between user's tissues; i.e., they are not "bioresponsive", so that in order to implant the device in a manner sufficient to maintain a fluid-tight seal, the tissue around the stoma is severely pinched, obstructing blood flow. The loss of blood eventually causes tissue death and results in further surgery being required to remove the damaged tissue and to repair the stoma. Some other devices are difficult to clean and therefore permit waste to accumulate in tissue crevices, resulting in unpleasant odors and tissue irritation. All of these shortcomings of the art are addressed by the various embodiments of the new continent ostomy port.

When a stoma is tightly sealed for an extended period, such as a matter of hours, there can be a painful build-up of intestinal gasses, which are explosively released as a bolus when the stoma seal is breached. Previous attempts to filter such gasses have met with limited success, as the filter device could permit leakage to occur. Known devices also do not take into account adjustment or adaptability to account for pouch disturbances, which occur due to internal or external pressure changes. The new continent ostomy port has a number of structural features that permit it to overcome these and other disadvantages of the known art.

SUMMARY OF THE INVENTION

The new continent ostomy port described herein can be non-surgically inserted into a new stoma or non-surgically retrofit into a patient who has an existing ostomy, and provides the ostomate with greater freedom of movement without the untoward results often associated with use of conventional devices. The new ostomy port permits long-term (at least 30 days) port access and eliminates the need to continuously wear an ostomy bag and/or the need for lengthy daily irrigation procedures. This long-term access port prevents the leakage sometimes associated with the use of irrigation devices and colostomy bags because the connection between such ostomy accessories and the patient is via the new locking, sealing port. Conventionally such accessories are connected directly to the stoma site by gluing or belts, thus permitting leakage because a complete seal at the site of connection is not always possible.

In view of the various short-comings of the known art, it is among the several goals and advantages of the present invention to provide a continent ostomy port ("COP") i.e. a port which permits the ostomate to be effectively continent, which virtually eliminates leakage of liquid and solid waste from the stoma, and which continuously controls gaseous odors by permitting gradual filtered release of intestinal gasses. The new device, having the features mentioned, is adapted to be selectively connected to a pouch or tubes, as may be necessary from time to time to dispose of waste and to irrigate the intestine for cleanliness and health, while also being capable of being tightly capped for substantial periods of time, even hours, for example, to permit the user to engage in normal physical activities and to function in a wide variety of social settings without fear of accident or embarrassment.

Because an external pouch is not required to be worn, and there are no belts, adhesives or other additional devices required to hold the new COP securely in place, the user has the freedom to wear tighter or more revealing clothing than would otherwise be possible, and there is no concern of noises, such as "crinkling" sounds, inherent with the usual plastic ostomy bags. The user thus is provided with a generally improved quality of life, including enhanced body image, increased confidence and potential sexuality, and has available a wider potential range of movement, enhancing possible athletic activities as well, without the psychological stress of concerns with leakage and odor. The new device is, however, adapted for selective use with new, specially designed, drain tubes, irrigation sets and optionally biodegradable, disposable waste bags, as well as with known styles of drainage tubes. In addition, the device works with known internal surgically created reservoirs, such as those generally known as Kock and Indiana-type pouches. It is also suitable for use with surgically formed urinary and bowel ostomies, as well as with cecostomies, and gastrostomies, and for decompression and irrigation purposes.

It is further among the advantages of the new invention, having the features indicated, that because of the presence of the catheter portion of the new device in the stoma, there is reduced likelihood of stoma prolapse to the outside of the abdomen, as well as reduced incidence of stoma retraction into the abdomen, and reduced likelihood of strictures in the stoma. There is the further advantage that there is no peristomal skin trauma from heavy colostomy bags and irritating adhesives, and the expense and bother inherent with use of pastes, glues, tapes and belts ordinarily required to keep a conventional stoma and pouch in proper placement is virtually eliminated. The skin to port seal developed in use of the continent ostomy port described herein is not impacted by cutaneous mucous discharge or topographical changes of the user's body due to weight gain, weight loss or aging, for example. An improved seal and compatibility with irregularly shaped or contoured stomas is readily accomplished with the new COP as compared with the art. Such improved sealing is seen even with use of the new device in ostomate patients who are elderly or obese, with soft or flaccid abdomens.

The indwelling nature of the new COP also has advantages for use in neonates or small children, because the neonate's skin is especially sensitive to the adhesives conventionally used for attaching a bag or sealing a stoma. The neonate is also well served by the lack of necessity for the constant presence of a colostomy pouch, because of the sheer bulk of the pouch that may overwhelm the tiny infant, literally inhibiting movement. The indwelling nature of the new COP is also ideal for ostomates who are undergoing skin-grafting, providing reduction in the otherwise high incidences of peristomal hernation and/or necrotizing enterocolitis ("NEC") seen in such individuals when fitted with conventional stoma pouch devices, because of the difficulties caused by the stoma environment, a surgical wound formed in the patient's abdominal muscle and the stapled skin over such an opening.

Thus, in furtherance of the above-mentioned goals and advantages, the present invention is, briefly, a continent ostomy port device having a generally planar face plate defining a selectively sealable aperture which is formed through and is alignable with the opening of a stoma formed in the body of a user of the device when the generally planar face plate of the device is disposed substantially parallel to the body wall of the user, over the site of the stoma, to thereby provide access to the inside of the stoma. A closure portion is connected to the generally planar face plate adjacent to the aperture and is adapted to permit selective and repeatable covering and uncovering of the aperture in the generally planar face plate. A catheter portion of the device has a first end and a second end, the first end being connected to and extending from one side of the face plate. The catheter portion extends proximally and the second end of the catheter portion is disposed interior of the user's body, within the ostomy site when the port device is in normal use position. The catheter portion has a continuous and generally cylindrical exterior side wall, and a continuous, generally cylindrical interior side wall defining a major lumen, which extends continuously from the aperture in the generally planar face plate to the second end of the catheter portion. The catheter portion is sized and shaped appropriately for non-surgical insertion through a stoma to a sufficient distance that the presence of the catheter portion within the stoma provides a physical barrier which reduces the incidence of stoma prolapse, without the use of extraneous, externally applied materials or additional surgery.

The invention further includes, briefly, a removable cartridge that is sized and shaped to fit snugly and slideably within the major lumen of the catheter portion of the device so as to be liquid-tight and to thereby prevent inadvertent escape of body waste material from the stoma through the device when the cartridge is in place, so that the user is not required to wear an ostomy bag. and to further thereby clean the interior side wall of the catheter portion as the cartridge is pressed into the major lumen of the catheter.

The invention also includes, briefly, a selectively operable anti-reflux valve that is attached to the second end of the catheter portion, to thereby permit blockage of the major lumen of the catheter portion by activation of the anti-reflux valve when it is desired to prevent escape of body waste through the port device, and to permit passage of fluid or solid material through the port device when the anti-reflux valve is deactivated.

The invention also includes, briefly, retaining structure that is connected to the catheter, and which is non-surgically, snugly fittable into the stoma, and thereby causes the port device to be self-retaining in a normal use position within a stoma of the user, without the need for special surgery and extraneous, external fixation materials such as tape, belts, and adhesives.

The invention is further, briefly, a pad for use with a continent ostomy port includes a body portion defining an aperture appropriately sized to place around the catheter of a continent ostomy port. The body portion of the pad is sized and shaped for placement against a user's skin beneath a face plate of the ostomy port. The pad is formed of a soft, flexible material to thereby cushion and protect a user's skin from contact with the ostomy port face plate, wherein the pad body portion has a distal surface which is domed and provided with a central indented region to thereby accommodate the distal portions of the continent ostomy port.

These and other advantageous features of the present invention will be in part apparent and in part pointed out herein below.

BRIEF DESCRIPTION OF THE DRAWINGS

FIG. 11 is a sectional, schematic view showing an alternative embodiment of the continent ostomy port of FIG. 1 inserted into a section of bowel (as one example only) to illustrate the COP retention function of the bolster, and with the closure member in the closed position.

FIG. 12 is a longitudinal sectional schematic view of the device of FIG. 11, with the closure portion open, illustrating an anti-reflux valve in operative position, and showing an alternative foam-style retention bolster before expansion.

FIG. 18 is a longitudinal sectional schematic view of an embodiment of the device of FIG. 11, with an obturating device in position, showing the continent ostomy port device extended for insertion into a stoma.

FIG. 19 is a longitudinal, partial sectional, schematic view of the device of FIG. 18, closed and illustrating the alternative bolster design in operative position.

FIG. 20 is a cross-sectional schematic view of the bolster portion of the device of FIG. 18.

FIG. 24 is a partial schematic, longitudinal sectional view of an alternative structure for the distal end of the catheter portion of the device of FIG. 1.

FIG. 25 is a partial schematic elevational view of an irrigation set connector adapted for connection to the COP of FIG. 24.

FIG. 26 is a partial schematic elevational view of an obturating cartridge adapted for use with the COP of FIG. 24.

FIG. 28 is a schematic top plan view of a moisture baffler shim constructed in accordance with the invention.

FIG. 29 is a sectional view taken on line 29—29 of FIG. 28.

FIG. 30 is a sectional view taken on line 30—30 of FIG. 28.

Throughout the drawings like parts are indicated by like element numbers.

DESCRIPTION OF PRACTICAL EMBODIMENTS

Figure 1:
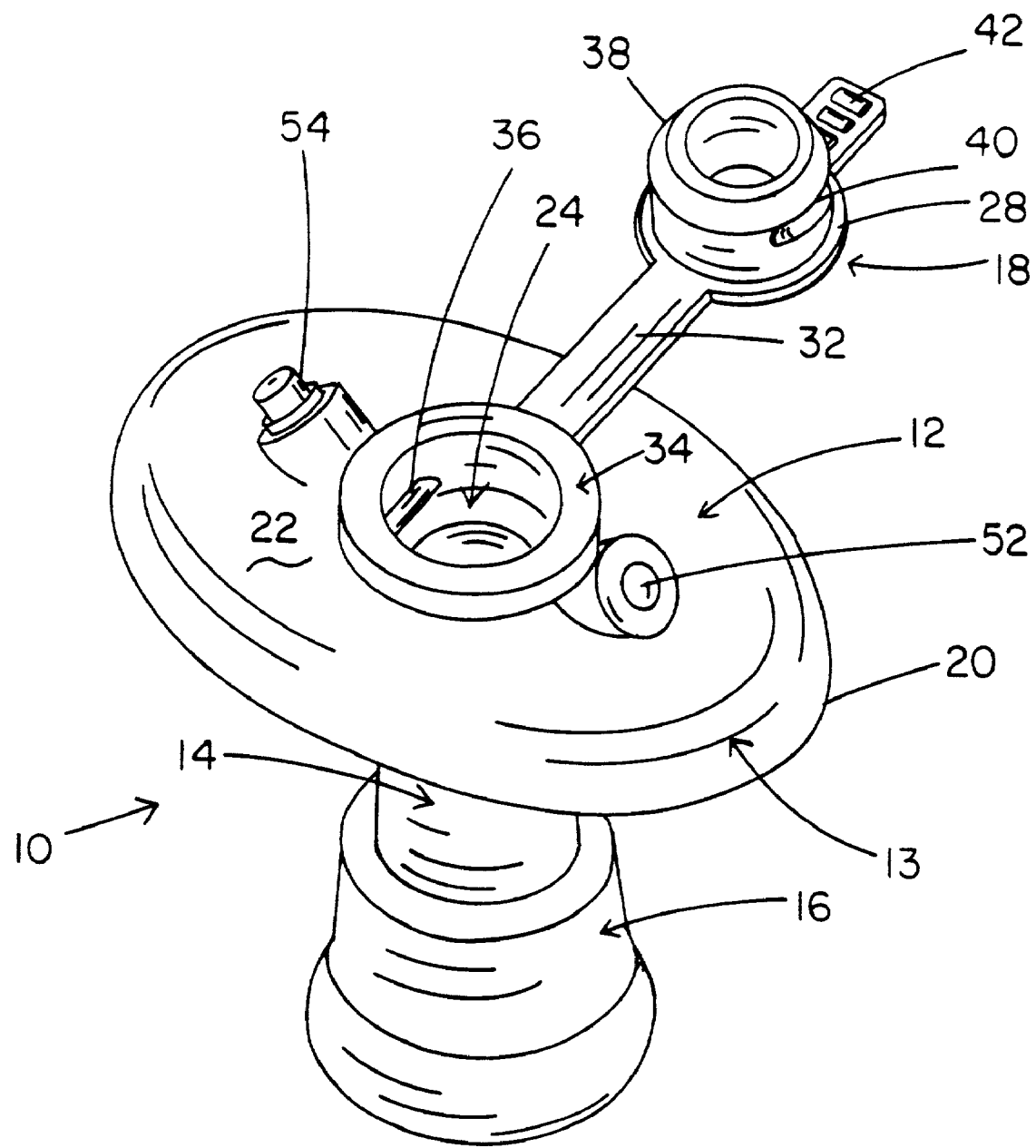
FIG. 1 is a perspective view of a new continent ostomy port device constructed in accordance with and embodying the present invention, and shown with the cap portion in the open position.

With reference to the drawings, and particularly, FIGS. 1, 2, 5, 6, 17 and 22, element number 10 generally designates a self-retaining continent ostomy port device ("COP") constructed in accordance with and embodying the present invention. The new ostomy device 10 is composed of a stomal disk or face plate 12 from one substantially planar surface of which there extends a catheter portion, generally designated 14, for indwelling penetration of the stoma of the user, the "ostomate", and non-surgical insertion into the intestine, or other body organ which has been subjected to an ostomy procedure.

A closure portion, generally designated 18, permits selective, openable covering of the distally disposed opening of the catheter through the stoma plate 12, and an internally disposed bolster or retention device, generally designated 16, maintains COP 10 in the necessary, implanted, operative position without the use of revisionary surgery or extraneous, externally applied materials such as belts, or adhesives. Bolster 16 may take a variety of forms, several embodiments of which will be described hereafter with reference to the drawings. All portions of COP 10 are formed of pliable, biocompatable materials, such as a sterilizable thermoplastic of known variety, such as polyurethane, for example.

Throughout this discussion the terms "proximal" and "distal" are used in the conventional medical manner; i.e., "distal" meaning farthest from the center of the body, and "proximal" being in the opposite direction, and are used in relation to the position of the claimed structure when new ostomy port 10 or various embodiments thereof are in operative position implanted in a stoma, as illustrated (as examples only) in FIGS. 11, 19, 21–21E, and, 27. Thus, "proximal" and "proximally disposed" are used in reference to the tip of catheter 14, which is inserted into the stoma, and the terms "distal" and "distally disposed" are used to indicate the opposite end of the catheter, at which opposite end there is connected, transversely to the axis of the catheter, the stoma face plate 12. As will be clear to one skilled in the art, after review of the following description, the new device 10 can be initially sized for an individual user and placed or "implanted" very easily in a clinic or office by a trained medical professional. Subsequent replacement ports 10, or parts thereof, can be inserted at home by the user (after minimal instruction), or by other trained individuals in alternate care settings.

The stomal disk or face plate 12 has a smooth perimeter 13, and is preferably elliptical, or oval, as shown, so as to fit more comfortably between horizontal skin folds. However, the face plate may take other shapes which may facilitate this fit or otherwise conform comfortably to the user's body, as long as there are no sharp corners or other irregularities that could be irritating to the wearer's skin, or catch on clothing. The generally planar extent of body 22 of disk 12 is sufficiently large to clear the stoma site circumferentially. Perimeter 13 terminates in a smooth lip 20, which preferably extends contiguously and proximally from perimeter 13 of disk 12, when COP 10 is in operative position, so as to entirely circumvent the exposed outer edge of the stoma.

Figures 2, 2A:
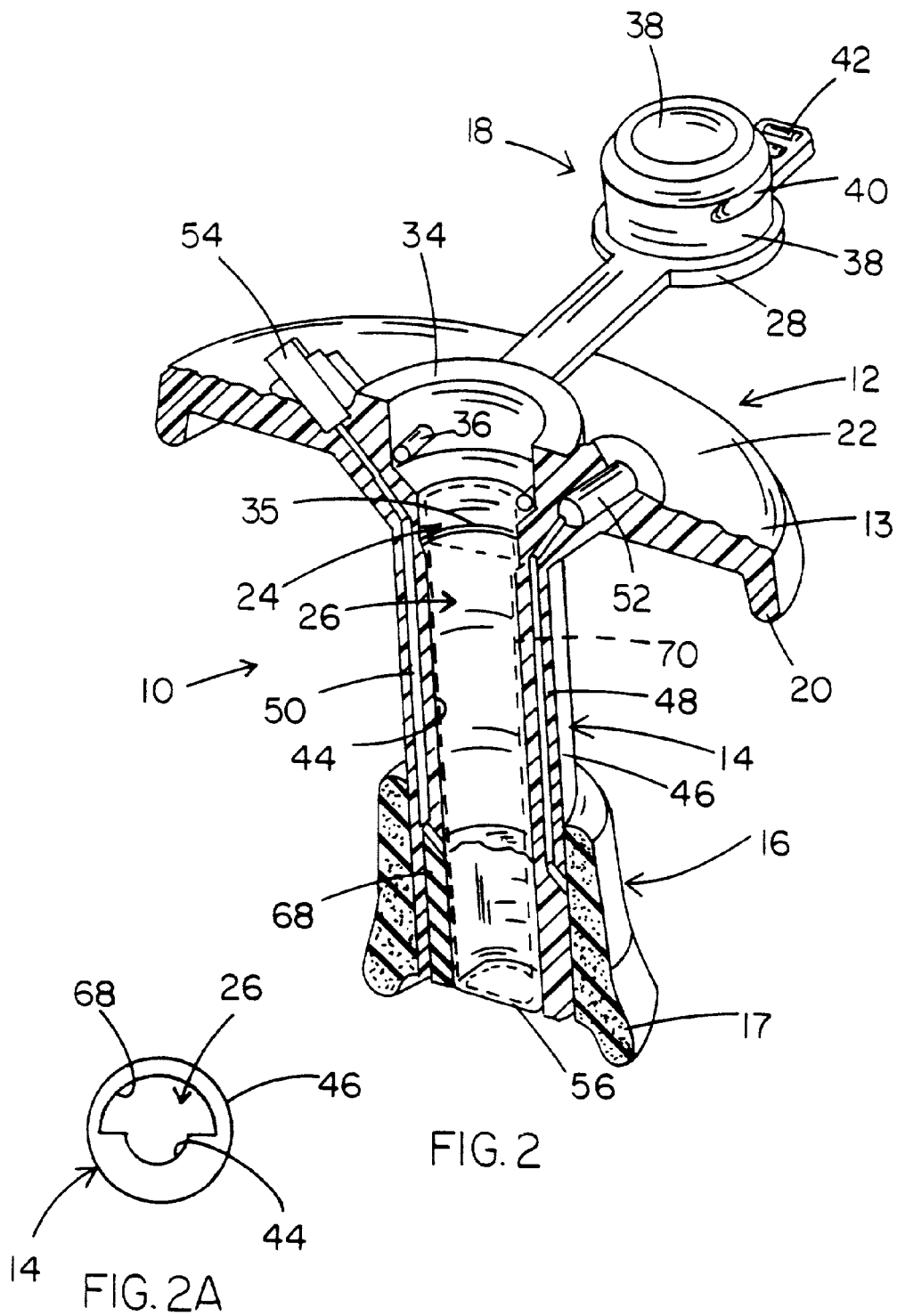
FIG. 2 is a vertical sectional view of the device of FIG. 1.
FIG. 2A is a transverse sectional, schematic view of the distally oriented end of the catheter portion of the device of FIG. 1.
Figure 3:
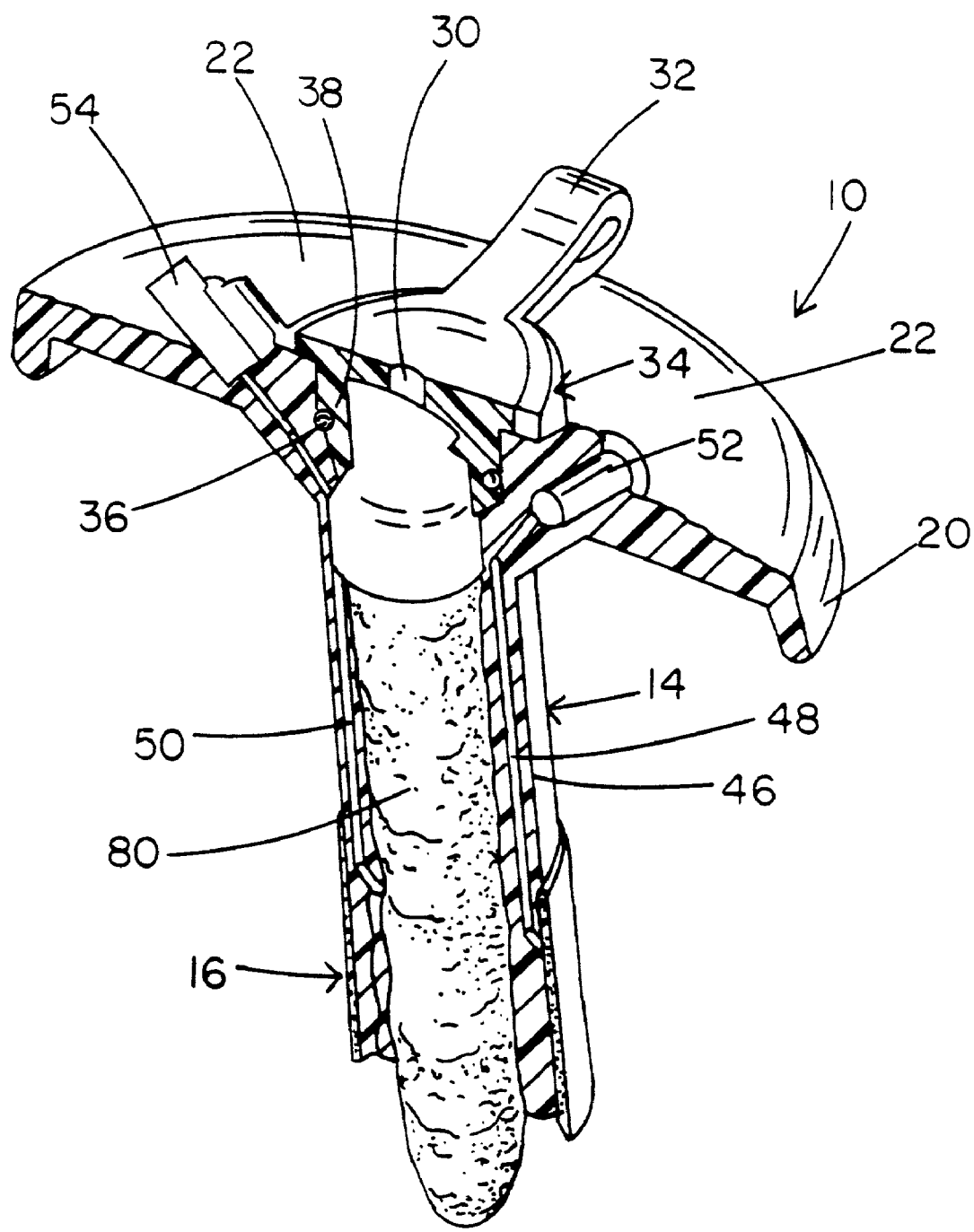
FIG. 3 is a perspective view of the continent ostomy port device of FIG. 1, in partial vertical section, with the closure portion in the closed position and including a cone-tipped obturating device inserted longitudinally into the catheter portion of the COP for placement of the device into a stoma.

FIGS. 1 and 2, for example, illustrate closure member 18 in an open position, and FIG. 3 shows the same structure in a closed position. Closure member 18 is preferably formed integrally with plate 12, but could be formed and applied separately to close the open distal end of catheter 14. As seen in FIG. 1, for example, the body of plate 22 defines an aperture 24, which is in open communication with a waste management lumen 26 of the catheter portion 14. Aperture 24 is preferably at the approximate center of the upper surface of the generally planar body 22 of plate 12. However, if necessary, or more comfortable for certain ostomates, aperture 24 could be offset from the center of plate 12.

Closure member 18 includes a cap portion 28 which is preferably flat, with an annular side wall, as shown, but may have a different shape, as long as the shape is appropriate for selectively openable sealing of aperture 24. A small vent hole 30 is formed entirely through the thickness of cap 28 to permit gradual release of intestinal gasses through port 10; even when cap 28 is closed. An elongated flexible retaining member 32 is connected at one of its ends to cap 28, and at an opposite end to a collar portion 34 of face plate 12, which collar portion 34, as shown, completely surrounds aperture 24. Paired detent bars 36 are formed on the inside of collar portion 34, preferably parallel to each other. An annular neck portion 38 extends from one surface of cap portion 28 circumferentially in relation to vent hole 30. Neck portion 38 is sized to be slideably, snugly received within collar portion 34, so as to be retained liquid tight therein.

In the embodiment shown in FIG. 1 paired detent grooves 40 are formed on opposite sides of neck portion 38 to engage detent bars 36 and thereby retain closure member 18 in the port sealing position illustrated in FIG. 3. Other possible structural configurations can certainly be conceived which will suffice for facile retention of a closure member over the opening of lumen 26. Such other configurations for a closure member are considered to be in keeping with the invention if other aspects of the invention are met.

It is also desirable to provide an integral finger grip 42 on cap portion 28, and particularly preferred that the grip 42 have ridges or other structure and be of sufficient size to enhance gripping, to enable an ostomate to readily and securely grip and pull it to remove cap portion 28 from the seated or closed position shown in FIG. 3 to the open position shown in FIGS. 1 and 2. This feature of course is a convenience and port 10 will function even lacking grip 42 altogether, or if such grip is modified in any of a number of ways which will be readily apparent to the skilled artisan.

Although the described closure structure is preferred, other useful closure means can certainly be conceived which will suffice. For example, the detent mechanism can extend entirely around the neck and corresponding bolster members, as illustrated schematically in the variations of an alternate embodiment, generally designated 100, shown in FIGS. 11–16, for example. In this embodiment an annular groove 140 is formed around the inside wall at the distal end of catheter 114. An annular ridge 136 on neck 138 of cap portion 128 is correspondingly sized to snap-fit into ring 140 in secure, leak-free, detenting fashion. Alternatively, the mechanism shown in FIG. 1 can be modified to use only one, or more than two sets of interacting, detenting bars and grooves. Similarly, the shape and structure of closure member 18 can be satisfactorily altered, as long as there is a mechanism provided to prevent inadvertent detachment and/or loss of the cap portion of the closure, so that the new continent ostomy port can always be selectively "closed".

Catheter member 14 is preferably generally tube-shaped and usually extends substantially perpendicularly to the plane of plate 12. However, catheter 14 is shaped and sized in diameter and length appropriately for the particular type of stoma for which the new COP is intended, it being understood that the new port is suitable and readily adapted for various types of ostomies and to any size of ostomate, as discussed in the Background portion above. Ordinarily the outside diameter of catheter member 14 will not be so large that the port device 10 cannot be gently manually turned or "twirled" within its seat in the stoma. The cylindrical, inner side wall 44 of catheter 14 defines a "major" lumen 26 and is most commonly straight and smooth to facilitate insertion and removal of a deodorizing cartridge or tampon 70, 70' (described further below) and to deter accumulation of particles of waste.

The exterior side wall of catheter 14 is also preferably cylindrical, smooth and straight. However, there certainly may be uses of port 10 conceived for which an altered shape of the catheter portion may be beneficial, without such altered shapes being outside of the scope of the invention.

In the embodiment of FIG. 2, COP 10, there are formed longitudinally within the material of catheter 14, between walls 44, 46 one or more elongated air ducts or minor lumen, such as those indicated at 48, 50, for example. How many such lumen are provided the exact structure of which will vary depending upon the type of bolster provided on a particular COP, as well as with the type of anti-reflux valve ("ARV") used, if any.

Lumen 48 exits proximally through the exterior side wall 46 of catheter 14, and is in fluid communication with bolster portion 16. Whereas lumen 50 exits proximally through the interior side wall of catheter 14, to open into the larger, major lumen 26, and/or is operatively connected to an anti-reflux valve 56. The distal ends of lumens 48, 50 both exit through plate 12, as illustrated, or in equivalent manner. The exterior access to lumen 48 is via a "breather" port 52, which provides a pressure relief mechanism for retention bolster 16. Port 52 is preferably provided with a filter or screening membrane (not shown) in such manner as to be open to the flow of gasses, but not to liquid. Exterior access to duct 50 is via inflation/deflation valve 54, which provides a means of operating anti-reflux valve 56, as discussed further hereafter.

By contrast, in COP 100, the embodiment illustrated in FIGS. 11–14 and 18–20, there is seen only one such air lumen 50, connected from access valve 54 to the anti-reflux valve 56', discussed further hereafter.

Figure 4:
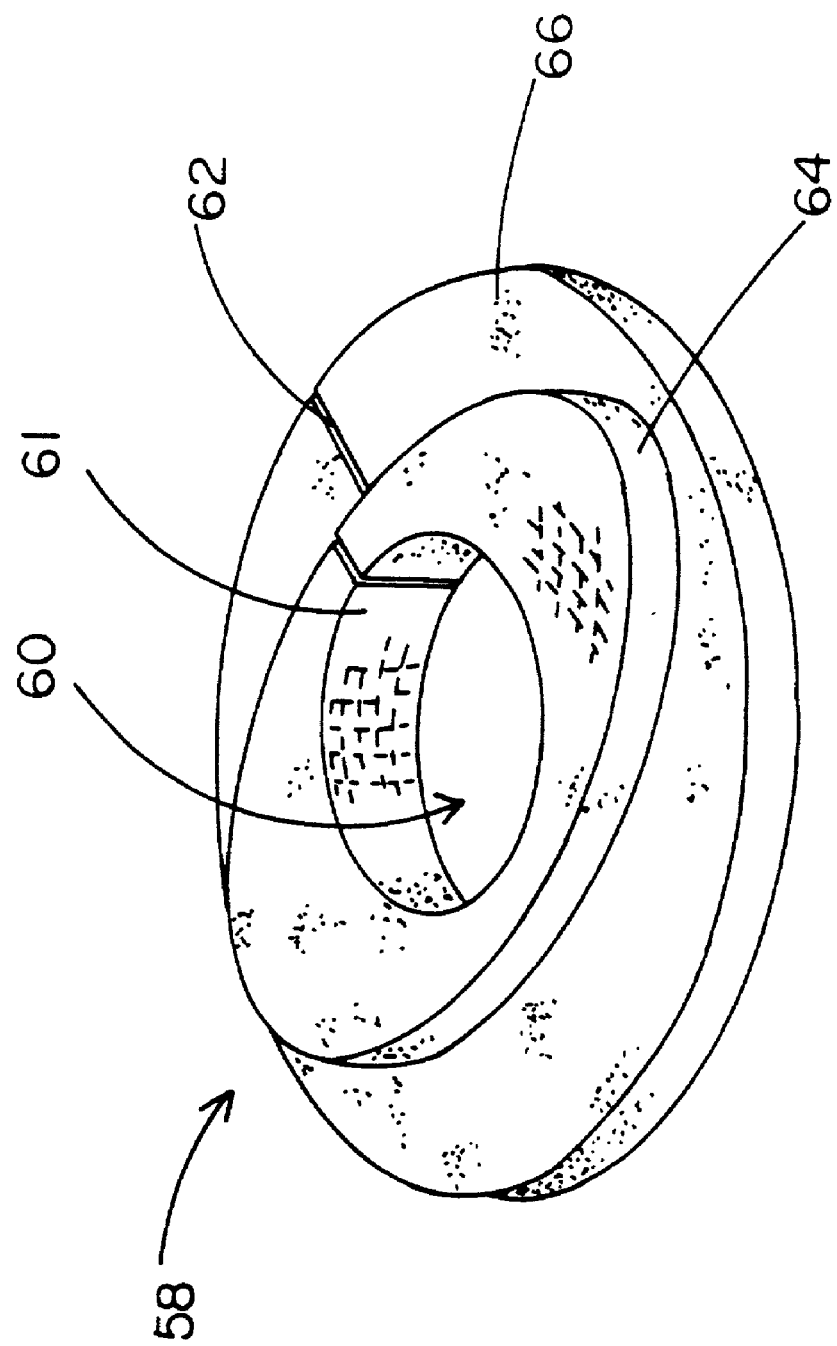
FIG. 4 is a perspective view of a moisture barrier pad, for optional use with the device of FIG. 1.

FIG. 4 illustrates a moisture seal or pad 58 (enlarged), which is preferably disposed in use between the back side of plate body 22, and the ostomate's body, covering the skin immediately around the stoma and serving to keep the stoma moist, as is necessary to protect the sensitive peristomal skin and stoma area. Pad 58 also provides some cushioning between the skin and lip 20 of plate 12 and is preferably formed of an open-celled foam into an oval shape with two substantially flat, stepped levels, although a single thick layer would suffice. A central aperture 60 is defined by a generally annular inside wall 61 and is accessible via slit 62, which permits the user to gently open the pad for facile placement to and removal from an operative position, entirely around the perimeter of the stoma T', as indicated in the sectional view of FIG. 11. It is expected that various sizes of pad 58 will be provided, depending, among other things, upon the user's size. For example, pad 58 can be made with the aperture 60 increasing in ¼ inch increments, from approximately 1 inch to about 2¾ inches.

Figure 5:
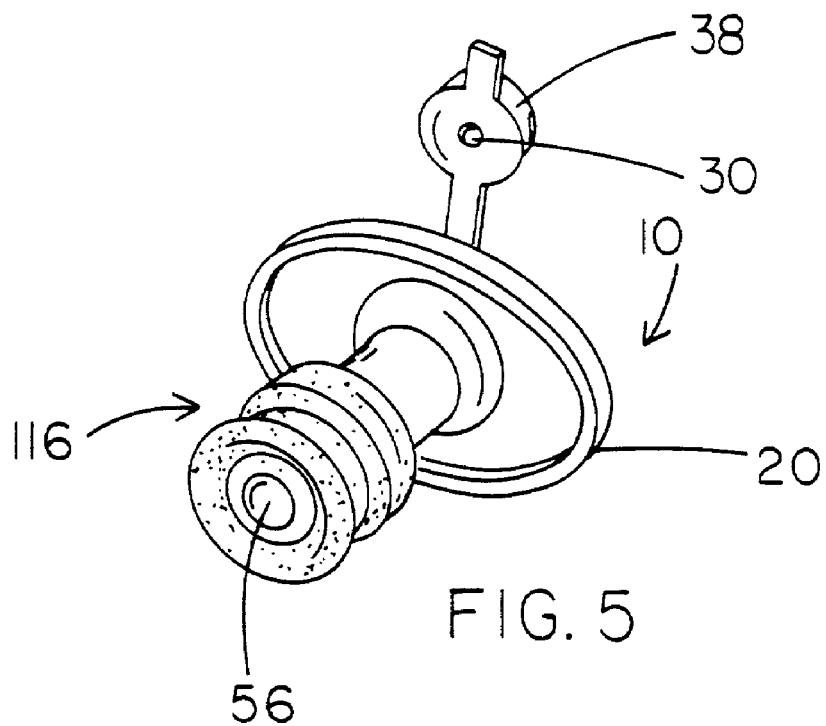
FIG. 5 is a back perspective view, reduced, of the continent ostomy port device of FIG. 1.

A first level 64 of pad 58 is formed with a perimeter slightly smaller than, but having the same general shape as the perimeter 13 of stoma face plate 12, so as to be readily fitted within the perimeter outlined by face plate lip 20, and to lie substantially flat and parallel to and between plate 12 and the user's skin. FIG. 5 illustrates the hollowed-out, proximally disposed side of stoma plate 12 (reduced), within which the first level 64 of pad 58 fits. With pad 58 so positioned, a second level 66 extends parallel to first (distal) level 64, and the perimeter of second level 66 extends somewhat beyond the first level, beneath lip 20 of plate 12, as indicated by broken lines in FIG. 6, to protect the user's skin from friction irritation.

The shape of the perimeter of second (proximal) level 66 of pad 58 may be generally oval, round, or otherwise, as however is economical and convenient to manufacture and comfortable to use, and which is functional as described with regard to the shape of the particular form of port 10. Likewise, if plate 12 is not substantially flat, but instead takes some other form, such as being arched, domed, or whatever suits the particular clinical circumstances, then pad 58 can be modified accordingly to fit beneath such modified plate shape. Thus, pad 58 provides a moisture barrier, which prevents the natural stomal secretions from drying, yet, as explained below, simultaneously serves to keep the skin around the stoma site dry. If desired, pad 58 also provides a handy means of medicating the stoma and the skin directly adjacent to the stoma, by simply applying medicated ointment, lotion, or the like to the proximally directed flat surface and annular wall 61 of pad 58, just prior to positioning the pad between the stoma and stoma plate 12.

Pad 58 is intended to be disposable, for maximum sanitary usage, and is designed to be inexpensive and simple to use, to encourage the user to change the pad on at least a daily basis. However, it is conceivable that pad 58 could be formed of material which is suitable for repeated washing and drying prior to reuse. It is further conceived that pad 58 will be formed of material that wicks moisture away from the skin surface, toward the face plate of device 10, to reduce fungal growth or other skin irritants. The outer, or distally disposed surface of pad 58, however, may be coated with a thin, liquid impermeable skin or membrane which will trap such wicked moisture within the pad, so as to prevent the user's clothes from becoming wet at the site of the stoma. If desired, or necessary the liquid impermeable skin may be of a type that is permeable to air, to permit the pad area to "breathe". To further enhance the flow of air to the skin around the stoma, the generally flat surface of face plate 12 can be provided with formed vent holes, not shown.

The inside wall 61 of pad 58 may also be provided with such a skin to prevent the stomal secretions from being absorbed into the pad. Depending upon the individual ostomate's personal conditions, it may be desired to have the pad coated on the distal surface, allowing skin moisture to be absorbed into the pad, and permitting such pad absorbed liquid to flow out of wall 61, but not out of the distal surface of the pad. In this manner absorbed body moisture is retained in pad 58 to keep the stoma from becoming overly dry. If desired, a layer of removable adhesive may be applied to the distally disposed side of pad 58, to maintain the pad in its desired position in relation to face plate 12.

Returning to FIG. 2 there is illustrated in longitudinal section, and partially broken away, inflated, one practical embodiment of anti-reflux valve 56, previously mentioned.

FIG. 2A illustrates in transverse section the semi-circular notch 68, in the proximal end of catheter 14, into which balloon valve 56 collapses when not activated. This embodiment is merely a repeatedly inflatable and deflatable cylindrical balloon structure that collapses upon deflation into a seat or depressed area 68 of lumen 26 of catheter 14, preferably but not necessarily at the extreme proximal end thereof, as shown. Anti-reflux valve 56 is in fluid communication with and is connected by lumen 50 to an inflation/deflation valve 54 (indicated schematically in FIG. 2), located on the outside or distal surface 22 of stoma plate 12. When activated, or fully inflated, ARV 56 blocks the proximal opening of lumen 26 to prevent inadvertent passage of intestinal contents from port 10. Typically, with the new COP, because of the presence of a deodorizing, filtration cartridge (to be described) in lumen 26, ARV 56 is in the non-activated, deflated, position, inflation (activation) only being necessary during certain hygiene procedures, as explained below. Thus, contrary to ARVs currently used in long-term medical devices, the new COP is capable of much longer wear without material fatigue or other break-down.

A variety of suitable structures are conceivable for purposes of providing an anti-reflux mechanism and the structure for permitting selective activation of the anti-reflux mechanism. In the embodiment shown in FIG. 2, inflation/deflation valve 54 is a schematic representation of a known Halkey-Roberts valve. By a such mechanism, or equivalents thereto, the user is able to selectively introduce air or other fluid into valve 54 via lumen 50, thereby inflating the valve balloon portion and blocking the proximal end of catheter 14 so that body waste does not inadvertently escape during certain necessary hygiene procedures, as further explained below. Likewise, the user can selectively withdraw fluid from valve 56, causing the previously inflated valve to collapse and let gasses or body waste pass into the lumen of catheter 14.

Figure 15:
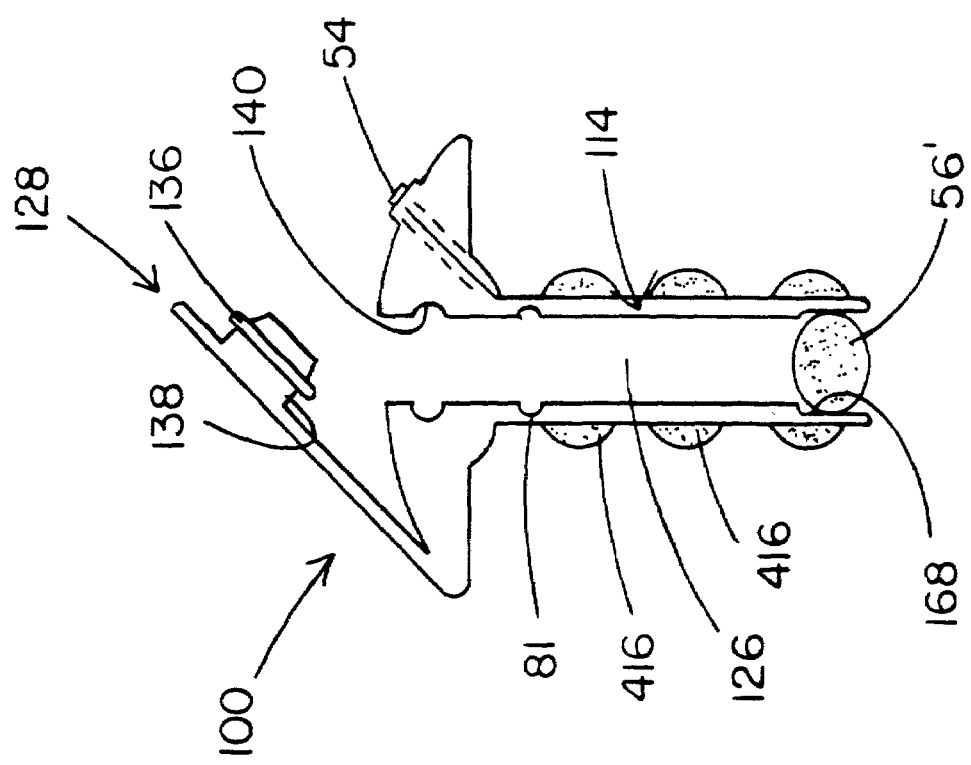
FIG. 15 is a longitudinal sectional schematic view of the device of FIG. 11, shown in the open position, with an anti-reflux mechanism in operative position, and showing a still further alternative style of foam retention bolster.
Figure 17:
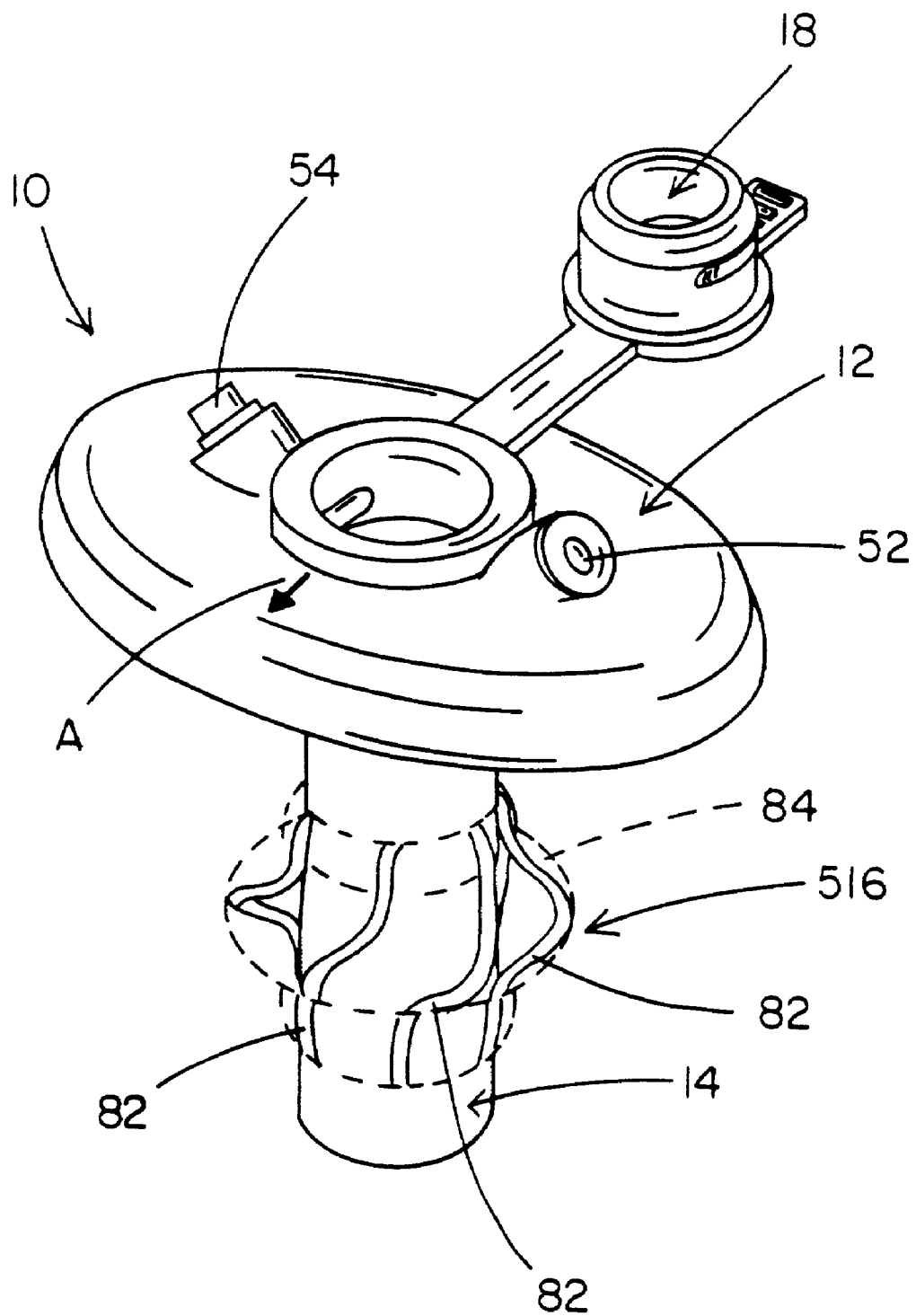
FIG. 17 is a perspective view of a further embodiment of the continent ostomy port device of FIG. 1, showing an alternative bolster design.

An alternative, spherical shape for the balloon/anti-reflux valve structure 56' is shown schematically in the second embodiment, port 100, as shown in FIGS. 12 and 15. In each case, inflation via introduction of air or other fluid through a small lumen is a suitable method for activating the valve to close off the proximal end of lumen 26. The above anti-reflux valve structures are offered by way of illustration only and are not intended to be limiting, as a variety of medical valve devices, both known and yet to be conceived, are expected to be suitable for use in the new continent ostomy port device, of either embodiment shown, or other reasonable variations thereof. Of course, the two anti-reflux valves illustrated and described herein in relation to port devices 10, 100 can be interchanged with respect to the port devices.

Figure 10:
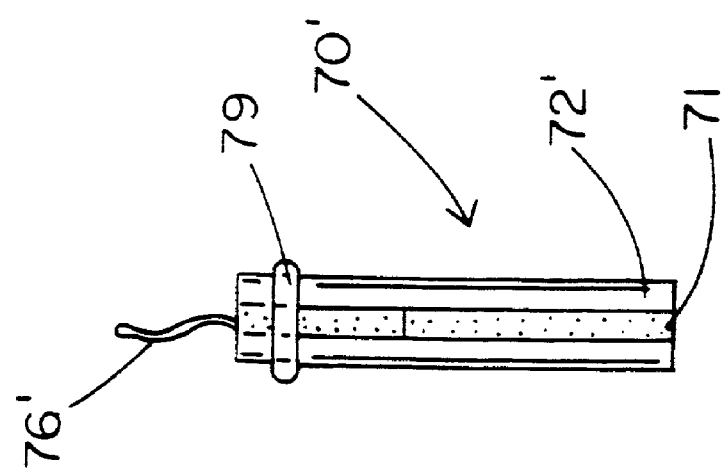
FIG. 10 is a longitudinal sectional schematic view of an alternative embodiment of the filtration cartridge of FIG. 9.
Figure 9A:
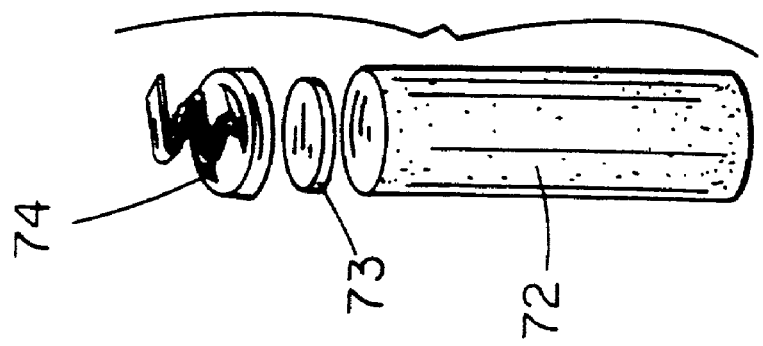
FIG. 9A is an exploded view of the odor control cartridge of FIG. 9 (not to scale), illustrating the optional placement of an odor control pellet beneath the end piece.
Figure 9:
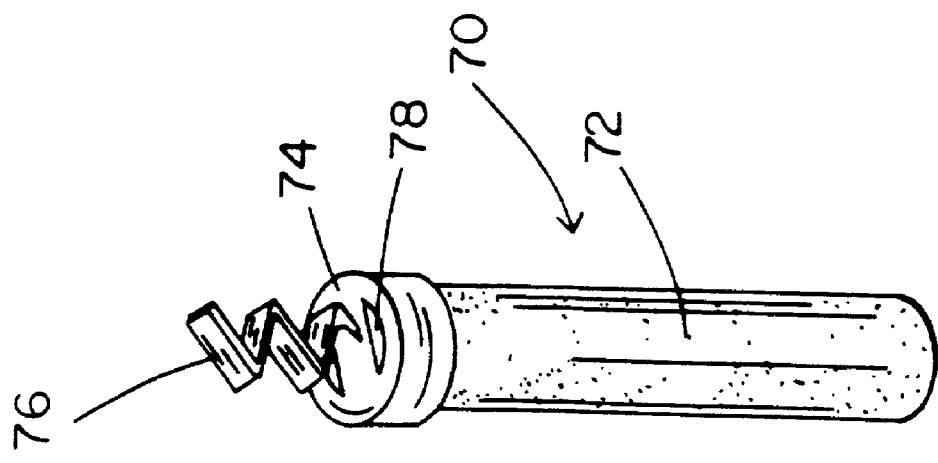
FIG. 9 is a perspective view of a filtration cartridge or tampon designed for use with the COP of FIG. 1.

FIGS. 9, 10 and 11 illustrate two of a number of practical constructions of an important aspect of the new COP 10, 100. Cartridge 70, shown in FIG. 9, consists of an elongated tampon portion 72 and a cap-like end piece 74. Tampon portion 72 may be formed of a biodegradable fibrous material, such as cotton fibers, for example, but alternatively, and preferably, is formed of a synthetic material, such as polyurethane, or a semi-rigid, breathable, closed-cell, moisture impervious foam. Cartridge 70 is preferably disposable, on at least a daily basis, and thus is formed at least in part of an economical substance, to encourage the necessary changes. However, cartridge 70 can also be made satisfactorily of materials which are suitable for washing and reuse, if desired, as long as the material is breathable, to permit passage of intestinal gasses therethrough, and not so readily biodegradable that it will not withstand operative placement in the new COP for an extended period, on the order of at least a day, or other normal wearing period.

Cartridge 70 is necessarily sized in diameter and length to fit slidingly and snugly coaxially within the inside cylindrical wall 44 of catheter 14, effectively blocking lumen 26 from the passage of solid and liquid wastes. Such snug sizing also provides cartridge 70 with a key function as part of the COP device, in that it permits cartridge 70 to act as a "squeegee", scraping clean the cylindrical inside wall of the catheter each time a new or fresh cartridge is placed into the catheter. This cleansing action of the cartridge is a feature not found in the known art. Further, the substantially constant presence of the cartridge within the catheter lumen prevents build up and encrusting of fecal material on the inside wall of the catheter. Thus, with known ostomy closures of the plug variety more effort is required to maintain the stoma area in a hygienic state.

Tampon portion 72 of cartridge 70 is especially preferably provided with an odor-absorbing or odor-neutralizing substance, such as activated charcoal, zinc, sodium bicarbonate, or other such known substances, so that cartridge 70 also provides a deodorizing function, as well as gas flow control and hygiene functions. In addition to the substances mentioned above, other odor absorbing compounds, including new ones, yet to be developed likely will also be useful, as long as they are safe for such intended use in humans. The deodorizing chemical used in cartridge 70 may be mixed throughout or impregnated into the material of the cartridge. Alternatively, as illustrated in FIG. 9A, the deodorizing chemical may be provided in the form of a pellet, or tablet 73, or other solid shape, disposed between the distal end of tampon 72 and end piece 74, or at some other convenient and useful point between the anti-reflux valve and closure portion 18.

The end piece 74 of cartridge 70 is formed of plastic, or other sufficiently durable, biocompatible material. A collapsible finger grip, such as that indicated at 76, for example, enhances gripping and removal of cartridge 70 when it is necessary to irrigate or drain the ostomy. Vent openings, such as that indicated at 78, or the like, are provided in cap 74, particularly if the material of which end piece 74 is formed is impervious to fluids. This permits the previously discussed gradual release of intestinal gasses when ARV 56 is deactivated (open) and cartridge 70 is in place in catheter 14 (as indicated in FIG. 2, in phantom, for example), even when COP closure member 18 is in the normal-use (closed) position. The diameter of end piece 74 (if any) is desirably greater than that of tampon 72, and thus is stopped from sliding too far into lumen 26 by the cap portion encountering and resting against a narrow, internal, annular shoulder 35 at the distal end of catheter 14.

FIGS. 10, 11, 16, and 19, as well as 21A and 21B show an alternate structure for the cartridge, indicated at 70', shown in FIG. 11 inserted into operative position in the second described embodiment of the new COP 100. Cartridge 70', and particularly the tampon portion 72' is shown somewhat reduced in diameter in the figures, for clarity. However, it is to be understood that to function optimally tampon portion 72', like tampon 72 has a diameter sized to fit snugly but slideably within the lumen of the corresponding COP catheter portion. The described snug, slideable fit is necessary to prevent leakage around the tampon, as well as to permit the tampon to serve the additional function of scraping or "squeegying" the internal cylindrical side wall of the catheter as the tampon is removed and replaced, preventing build-up of fecal material within the catheter.

As in the first embodiment, cartridge 70' also has an elongated cylindrical body or tampon 72', but includes a central longitudinal core 71 of deodorizing material, instead of the deodorizing substance being mixed throughout or impregnating the tampon material.

In this second cartridge example, end piece 74' is effectively merely a continuation of the tampon per se with an elongated, flexible filamentous member 76' connected for improved handling, and an annular ridge 79 extending outwardly, preferably entirely around the cartridge end 74', to act as a detenting mechanism, engaging an annular groove 81 within the distally directed end of alternative COP device 100, as illustrated in FIG. 11. This construction provides the user with a palpable "stop" point to help prevent accidental over-insertion.

Clearly, as with other aspects of the new continent ostomy port, various features of the two cartridge examples 70, 70' could be interchanged as desired, depending upon the embodiment of the COP chosen, or as required, depending upon factors particular to the individual user's situation. For example, cartridge 70' could be provided with a modification (not shown) of end piece or cap member 74, wherein an annular detenting ridge is provided on the cap member, rather than on distal end of the tampon per se. Other useful alterations in the deodorizing filtration tampon of the new COP will likely be apparent to the skilled artisan.

FIG. 1 illustrates one of a variety of potential forms for an internal retention mechanism or "bolster", generally designated 16, as conceived in the present invention. Among the varieties of bioresponsive retention mechanisms conceived for maintaining COP device 10, 100 in a comfortable, safe operative position are a number of configurations of foam "sleeves" or "cuffs", illustrated in FIGS. 1, and 11–16, and discussed hereafter, a thermo-sensitive wire-form variety illustrated in FIG. 17, and an obturatable variety illustrated schematically in FIGS. 18–20 and discussed hereafter. All of such bolsters are in keeping with the goals of the present invention and provide the advantage that the new continent ostomy port can be held in place comfortably and reliably, without leakage and skin abrasion or other tissue irritation, or necrosis, all without the use of belts, glues, adhesives, and without any other body external mechanisms or surgery. Thus, the new COP relieves the previous problematic causes of skin abrasion in ostomates, the chronic compression of tissue and related vasculature.

In each case, the bolster holds the COP in operative position by pressure placed by the bolster, radially from the longitudinal axis of catheter portion 14, 114 against the tissue generally designated T (of which the stoma is formed); e.g. the instestinal wall proximal to the stoma site. Thus, the internal tissue is gently pressed outwardly the bolster in what is effectively an entirely internal "press-fit" or "friction fit" of the bolster against the tissue. This operative structural fit of one style of bolster 316 is illustrated for example, in FIG. 11, and discussed further hereafter. Another example is shown in FIG. 19, with reference to bolster embodiment 616.

It is to be understood that the retention bolster styles of the new COP are referred to as "bioresponsive" because they perform the above-described reliable and secure site retention function without exerting damaging, excessive pressure against the surrounding tissue. It is necessary that the internal bolster does not dilate the bowel wall to such an extent that the vasculature is crimped or pinched. Excessive radial pressure to the lining of the bowel or other organ over any substantial period of time causes ischema and/or bowel necrosis.

It is considered normal in non-ostomates for the bowel wall and any other hollow organ to become routinely squeezed at times, due to a spike in the pressure exerted by nearby, overlying or adjacent organs and musculature. In the case of an ostomate with an indwelling COP device, this may happen during exercise, heavy lifting, sexual activity or even by merely coughing. When the stoma is pulled through a surgically created defect in the rectus abdominus muscles, any flexing of these muscles can also cause change in the internal pressure on the bowel wall. Accordingly, an internal retention bolster on a continent ostomy port, which is to be implanted for an extensive period of time, must be bioresponsive in order to accommodate such pressure changes by correspondingly changing and to thereby avoid tissue damage. The bolster must be dynamic in nature, in order to routinely adjust by automatically collapsing and re-expanding, depending upon the needs and position of the body at a given time. The various embodiments of the bolster portion of the new COP 10, 100 readily meet this challenge in a manner never before accomplished by the known art.

For clarity of the invention and simplicity of this discussion, the new COP device will be referred to by element number 10, the embodiment with closure portion 18 style, and 100, the embodiments with closure portion 118 style. However, it is to be understood that the retention bolster portion will vary among the different views and may conceivably be interchanged among the various practical embodiments of COP 10, 100, without altering the scope of the invention.

Further, the new COP generally; i.e. the plate and catheter portions may vary; i.e., in some views being schematically simplified, and not all elements will be shown in all views, which views are provided for illustrating the various forms of bolsters or other optional features and/or interchangeable features of the new COP. The various bolsters, described hereafter, are indicated as 16, 116, 216, 316 and so on. It is to be further understood that the bolster portion is a preferred aspect of the new COP; and is preferably, but not absolutely necessarily, bioresponsive. Rather, the combination of the described face plate and catheter portions, alone (and especially in combination with the described odor and waste control cartridge), is considered to be new, useful and non-obvious.

FIGS. 1–3, illustrate retention bolster 16 which is formed as a spongy, foam-filled cuff or sleeve which entirely surrounds and is fixed to the cylindrical outer side wall of catheter 14, toward the proximal end thereof, spacedly from the position of face plate 12, so that there is comfortable room remaining, a matter of about three cm to about 12 cm along the length of catheter 14, for receiving the surrounding stoma tissue. This preferred free catheter length also applies to the second embodiment, COP 100, for example as indicated in FIG. 19, wherein the stoma tissue beneath the face place 112 is indicated at T'.

In FIGS. 1 and 2 bolster 16 is shown in a pre-distended or expanded, operative shape. It is conceivable that bolster 16 may be implanted with this shape inherent. Alternatively and most commonly, bolster 16, as implanted, will have the shape shown in FIG. 3, a thin, flat sleeve, which is obtained from the normal bell-shape shown in FIG. 2 by pulling (e.g. by syringe) or squeezing (e.g. manually) air from the bolster.

Once implanted, ordinarily using a tool such as the cone-tipped obturating tool 80 shown in FIG. 3, the bolster swells, simply due to atmospheric pressure, returning to the original operative bell-shape shown in FIGS. 1 and 2. This selectively changeable expandable feature applies to all of the foam style bolsters described herein, and is due, in part to a thin casing preferably provided entirely over the outer surface of the foam bolster. Such casing, if any, may be formed, for example, of polyurethane which is not permeable to air, and thus will permit the user to selectively collapse the bolster by applying negative pressure via valve 52. Alternatively, but less likely, the casing or skin 17 of the foam type bolsters may be formed of cellulose, for example, of other material which is designed to break down on extended exposure to moisture, as within the stoma site, so that the expanded bolster shape will be maintained. Further, new "foams" are available and in further development, which will expand to a pre-designated shape, or to fill the shape, whatever it may be, of the cavity or area in which the foam is placed. Thus, it is conceived that the foam bolster portion COP 10, 100 will be pre-formed to expand to a specific shape that accommodates the blood vessel and/or muscle locations within the intestine in which the COP is implanted, for example.

Figure 6:
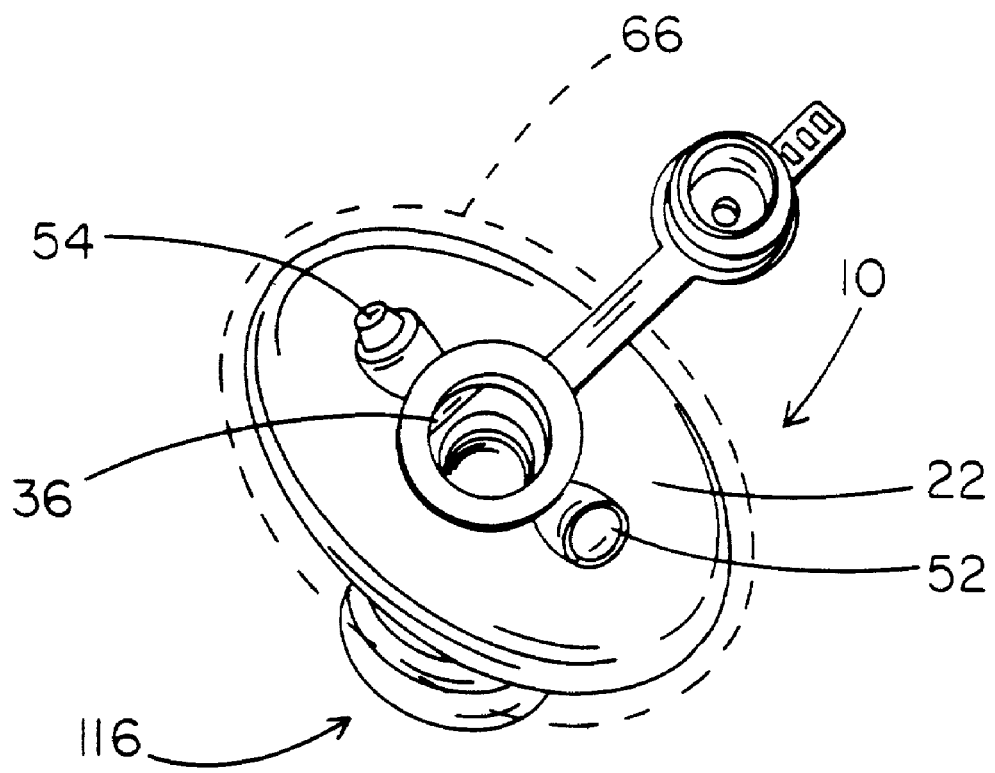
FIG. 6 is an upper perspective view of the device of FIG. 5, from a different angle than shown in FIG. 1, for clarity.
Figure 13:
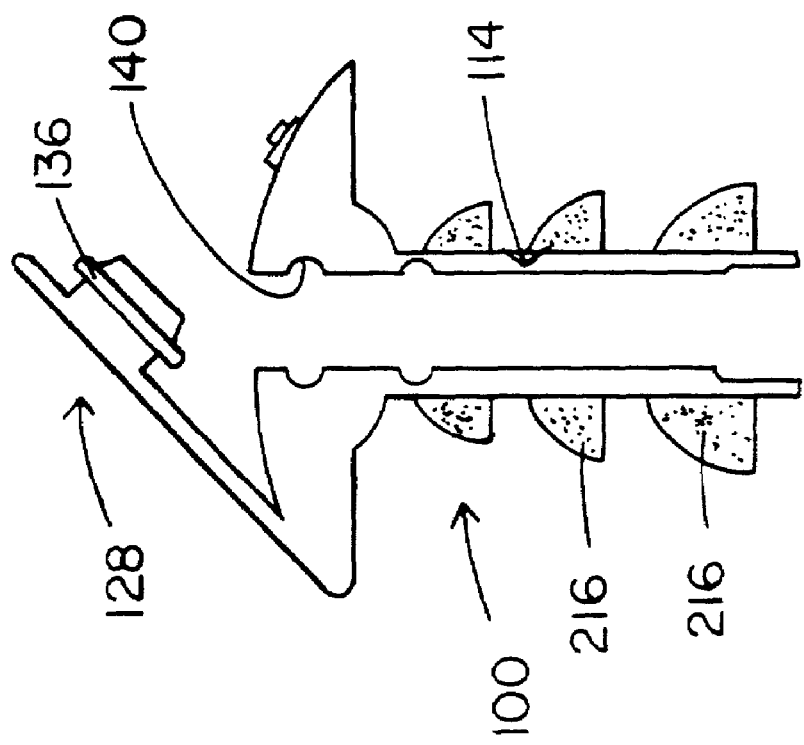
FIG. 13 is a longitudinal sectional schematic view of the device of FIG. 11, with an alternative form of retention bolster.

A variation of the bell-shaped bolster is indicated in FIGS. 5 and 6 at element number 116. FIG. 13 shows a variation of the foam style internal retention bolster, indicated at 216 and referred to as the shark-fin style, due to the appearance in section of the multiple arcuate foam "rings" which are fixed co-axially to the outer side wall of catheter 14. Although it is preferred to have at least two and preferably three such foam rings, only one bolster ring of this style will suffice for some situations, depending upon the type of ostomy and the patient's particulars. This bolster style is merely one example of such a bolster which can be pre-shaped and then implanted in such manner that expanded bolster portions fit snugly between the transverse, circular muscular rings within the intestine, to thereby secure the COP in a manner which is reliable, comfortable and bioresponsive.

Figure 14:
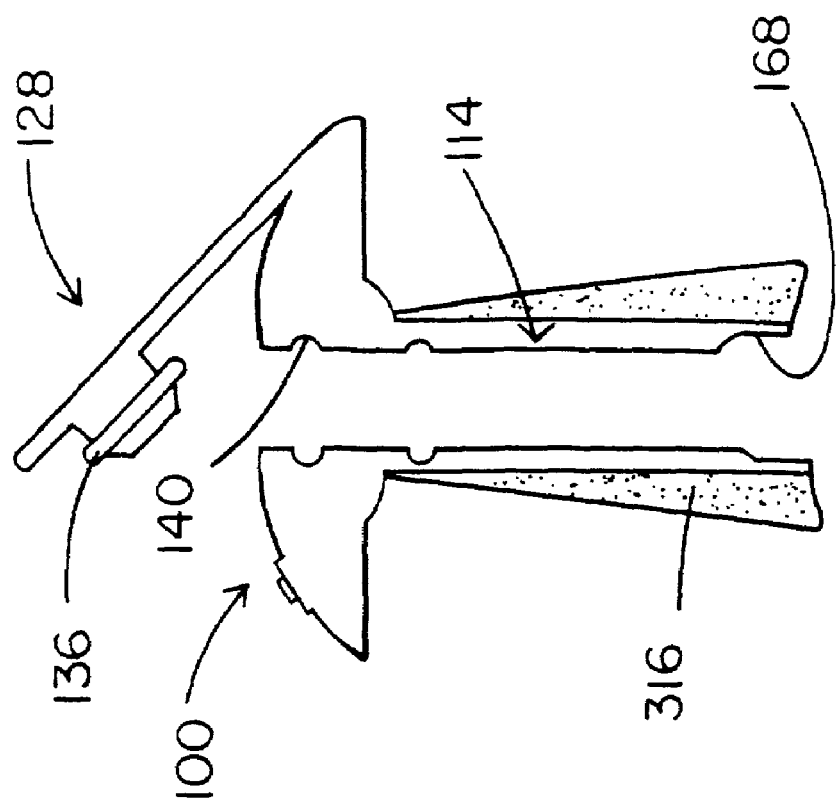
FIG. 14 is a longitudinal sectional schematic view of the embodiment shown in FIG. 11, but in the open position, without the filtration device.

FIGS. 13 and 14 illustrate foam bolster style 316, which is essentially a truncated cone-shape of the same material previously described, with the wide portion of the cone being disposed proximally. This style begins, pre-insertion, with a shape more or less like the foam layer shown in FIG. 12, coating the proximal portion of the exterior cylindrical side wall of catheter 114. Of course the foam layer 316 may be rougher or smoother, thicker or thinner, and of uniform thickness along the length thereof, or non-uniform, depending upon the specific material used and the final, operative bolster shape desired.

Figure 16:
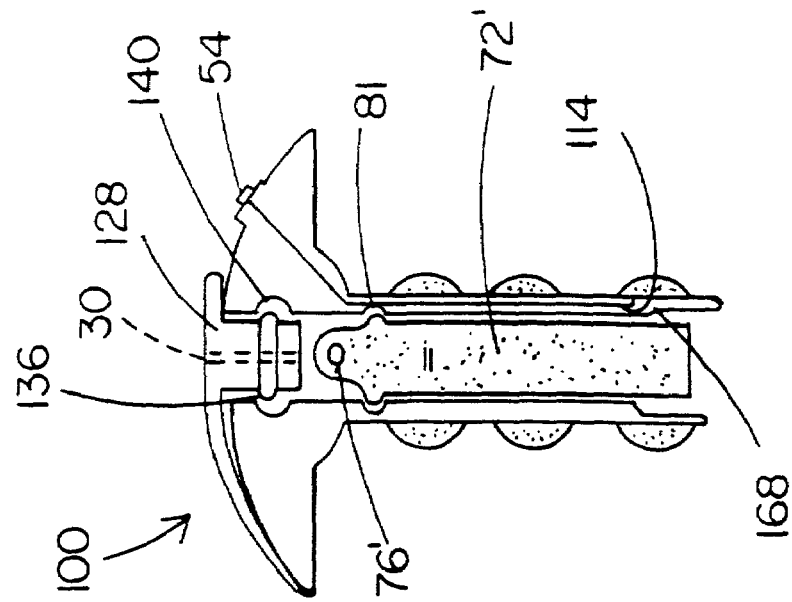
FIG. 16 is a longitudinal sectional schematic view of the embodiment shown in FIG. 15, in closed position, with a filtration cartridge in place, the filtration cartridge being shown with a slightly reduced diameter for clarity of the figures.

FIGS. 15 and 16 illustrate foam bolster style 416, which is formed as one or more doughnut shapes, or semicircles when viewed in cross section, surrounding catheter 14. As with the bolster version 216 of FIG. 13, while one such doughnut shaped bolster portion may suffice, it is ordinarily preferred to use more than one, to ensure a secure fit. Which of the above-described foam bolster shapes, or of the following further bolster designs, is selected will vary depending upon the patient and the type of ostomy. It is to be understood that the above constructions, and those which follow are intended merely as useful examples and the invention is not to be considered to be limited thereto, as other equally useful shapes may be conceived by the skilled artisan.

FIGS. 17 through 20 illustrate two varieties of a different type of internal retention bolster, also in keeping with the purposes and function of new COP 10. Bolster 516, shown in FIG. 17 consists of a series of twisted filaments or "wires" 82 fixed at both ends of each filament to the outer side wall of catheter 14, longitudinally in relation to the catheter and spaced apart from one another, preferably around the entire perimeter of the catheter. The number and size of filaments 82 will vary, depending upon the size of COP 10, the implantation site and the patient. As shown in phantom in FIG. 17, filaments 82 of bolster 516 may be (but are not necessarily) entirely encapsulated within a membrane or capsule 84 of soft, flexible sheet-like material, such as a type of polyurethane, for example, which is sealed at two ends thereof to the outer cylindrical side wall catheter 14, beyond the ends of filaments 82.

Filaments 82 may be formed of any suitable flexible material with sufficient material "memory" that the original bent shape of the filament will be sought after some deformation resulting from shifting in internal body pressures, so that the bolster is effective in keeping COP 10 in a secure leakage proof seat in the stoma. At the same time, the material of filaments 82 must be sufficiently pliable that the bolster will "give" as necessary to avoid tissue damage.

Thus, filaments 82 may be formed of certain plastics, either existing or yet to be conceived, and may also be formed of certain metals. In the case of metals, a number of known metals and alloys thereof are deemed suitable. However, the most preferred and commercially available metal of which filaments 82 are formed is a nickel-titanium alloy referred to as nitinol, a metal that is particularly suitable for this purpose due to characteristics such as pliability, kink-resistance, biocompatibility , shape memory, and fatigue resistance. Thus, in the case of the COP 10 shown in FIG. 17, wherein the bolster includes a plurality of filaments, (e.g. encapsulated wires 82 of nitinol), the filaments or "wings" can be pre-shaped and spaced according to the patient's particulars, including size and position of the intestinal vasculature proximal of the stoma. This embodiment of COP 10 may require an external orientation system, such as arrow A or other indicator applied to face plate 12 to ensure appropriate placement within the stoma. Once implanted, as part of the COP, when the patient experiences an internal pressure change, for example, from bending and lifting, filaments 82 of nitinol will bend out of the shape shown, in order to accommodate any bending and compressing of surrounding tissues, without creating increasing deflection force from the nitinol wires 82 as the wires become compressed within the body. Then immediately resume the illustrated shape when the user stands upright or otherwise shifts from the bending position, which initially caused the deformation.

FIGS. 18–20 illustrate bolster variety 616 in relation to continent ostomy port 100 (the anti-reflux valve not shown, for simplicity of the figures). Bolster 616 is shown in this instance connected to or formed as an integral extension at the proximal end of catheter 114. Bolster 616 is preferably formed at least in part of plastic, but may also be at least partly formed of metal or other biocompatible, resilient material. The cross-sectional view in FIG. 20 illustrates three support "spokes" 90 extending radially outwardly from catheter 114, and the flexible, sheath-like wall of bolster capsule 92 (not shown in FIG. 19, for simplicity). Two of such spokes 90 can be seen in FIGS. 18 and 19, longitudinal sectional schematic views. In FIG. 18 bolster 616 is shown as being forced into a spokes-extended disposition by a known obturating device 94. In this position COP 100 with the illustrated bolster 616 style is inserted into a stoma. The distal ends of extended spokes 90 are connected to one another by an annular connection piece 96. Once inserted deeply enough, with face plate 112 in substantially parallel and adjacent proximity to the stoma tissue T' obturator 94 is removed and spokes 90 resume the folded operative position illustrated schematically in FIG. 19. Note that in this embodiment, no "breather" valve is necessary. The valve and duct arrangement illustrated is for purposes of inflation/deflation of an anti-reflux valve (not shown) of a type previously discussed.

The new internal retention bolsters described above for COP 10, 100 are all bioresponsive in nature. Even though the expandable foam style cuffs are encased in a membrane, the system is not actually closed. On the contrary, air contained in and around the bolster can freely escape via the breather duct 48 and port 52, thus allowing the internal bolster to temporarily slenderize whenever the intestine demands that it should, due to a spike in surrounding abdominal pressures. (Further, the "wire" styles are also all designed to give as necessary. If desired, the wire styles can also be provided with a breather valve 52, as illustrated in the embodiment shown in FIG. 17 for example.) The described foam and wire/metal cuffs also abruptly re-expand to respective predetermined shapes and sizes as soon as the spike of intra-abdominal pressure subsides.

Figure 7:
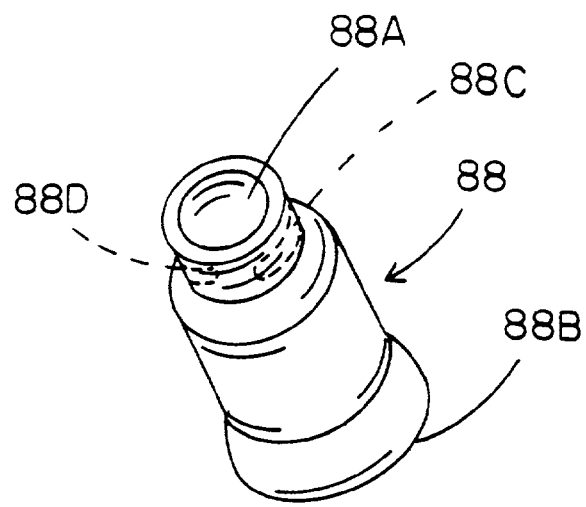
FIG. 7 is a perspective view of a connector for optional attachment of a waste bag to the device of FIG. 1.
Figure 8:
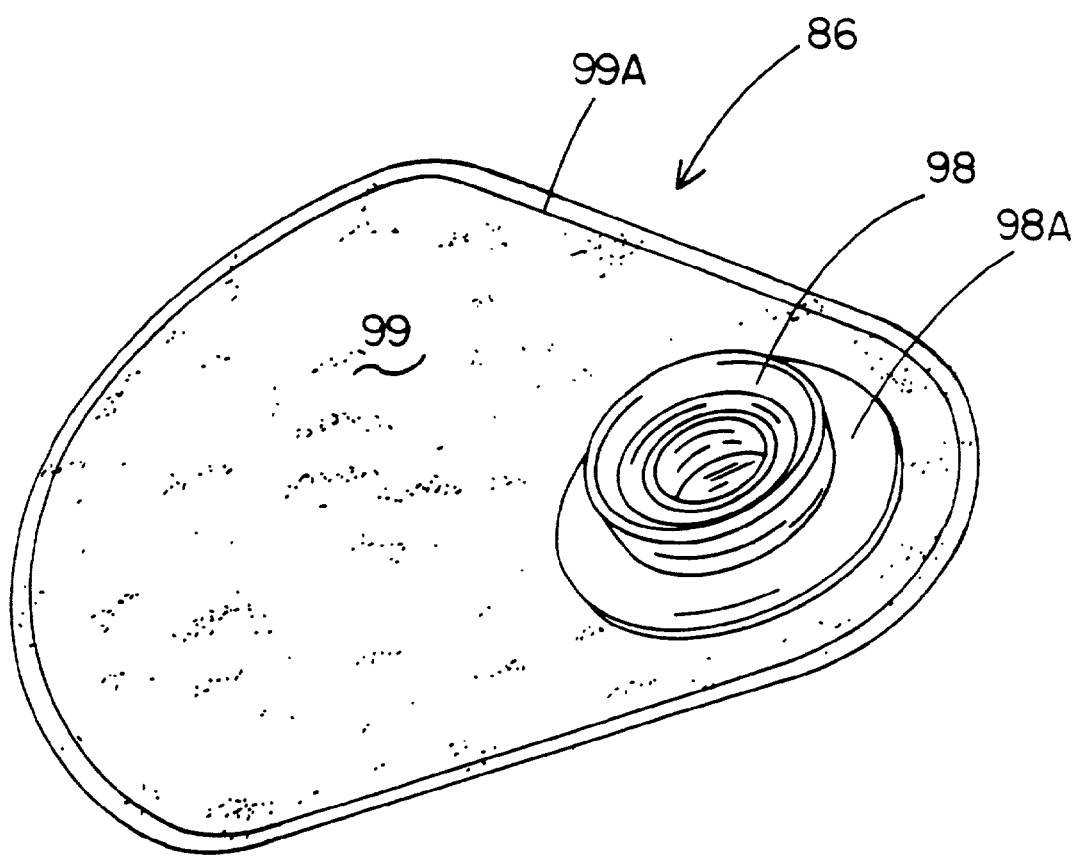
FIG. 8 is a perspective view of a waste bag designed for optional connection to the device of FIG. 1.

Among the various optional accessories that are conceived for convenient hands-free use with the new continent ostomy port device 10 is a flat bag or pouch 86, ordinarily intended for only occasional use, such as when intermittent drainage in remote locations is desired. A preferred embodiment for pouch 86 is illustrated in FIG. 8. FIG. 7 illustrates an example of an optional connector 88 for temporarily attaching pouch 86 to the distal end of catheter 14 as it opens through plate 12. For example, the small end 88A of connector 88 is inserted into the center of collar 34 of the new COP, and the opposed, larger end 88B of connector 88 is sized and shaped to fit, liquid-tight (although allowing passage of gasses), into a correspondingly shaped receiving member 98 which is attached by a flange 98A to one side of bag 86, as illustrated in FIG. 8. If desired, port connection end 88A can also have, for example, formed detenting ridges or grooves, indicated in phantom at 88C, 88D, respectively, as however corresponds to the structure internally of the collar of whatever style of collar, e.g. 34, 134 is in use in the particular device 10, 100 selected. Alternatively, receiving member 98 on bag 86 may be modified to connect directly to collar 34, 134 of the new ostomy port.

Collection bag 86 has a relatively flat or "low" profile when empty, consisting of two sheets 99 (only one of which is visible in the figure) of sheet-like material joined together in overlying relationship and sealed in a liquid tight manner, for example by heat sealing or adhesive along seal line 99A, preferably around the perimeter of bag 86. In keeping with the intention for pouch 86 to be used as the exception, rather than as the rule, it is relatively small as compared to conventional colostomy bags, having a volume of only up to about 200 cc. Further, preferably being formed of a natural fiber or other biodegradable material, bag 86 is suitable for flushing down a conventional toilet without undue risk of blockage of the sewage system.

Of course the precise shape, construction, materials and attachment of bag 86 may vary and remain within the scope of the invention for use in combination with the new COP. It is necessary, however, that the new ostomy pouch 86 be of small enough size that when fill it does not place undue strain caused by excess weight, on port 10,100. Further, pouch 86 must be adapted or have an appropriate connector such as 88, for liquid-tight connection to new port device 10, 100. When so constructed, it is very easy for the ostomate to connect bag 86 and to then go about the tasks of daily life as the bag fills.

By way of comparison, standard ileostomies have a very high output of fluid, generally producing and average of about 1,000 cc of highly corrosive matter daily. Previously, individuals with this type of ostomy, and who sometimes were not candidates for surgical construction of internal reservoirs, had no other choice but to wear pouches at all times. Due to the size and filled weight of these bags, it is often necessary for the user of such known pouches to also use some sort of belt arrangement to help to support the filling and filled pouch. No such extra support devices are required with the small, "low-profile" pouch of the present invention.

Since the stools produced by ileostomies are very loose and watery, they tend to be very difficult to contain. Leakage and skin trauma inherent with these leaks are consistently rated as the number one hardship facing ileostomates. The new COP 10 in combination with the new, liquid-tight, intermittent use, mini-drainage bags provides such normally young ileostomates with a long-awaited solution to permit a much more active life-style, and help to ensure that the new COP can accommodate most normal and emergency situations that an ostomate will encounter. No adhesives or belts and the like are necessary for the ostomate to take advantage of this hands-free convenience.

Figure 21A:
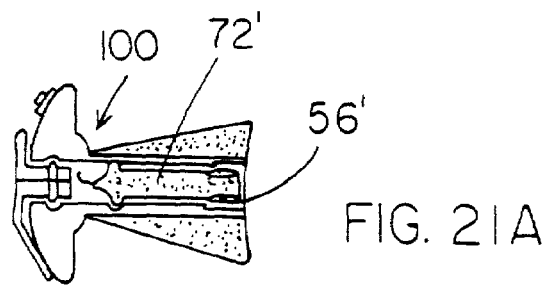
FIGS. 21A through 21E are a series of schematic illustrations provided to show the ostomy drainage and purging process performed with the new continent ostomy port.

FIGS. 21A through 21E illustrate an example of use of ostomy device 100. Identical steps can be taken with use of device 10. Generally, FIG. 21A shows device 100 with the closure member in closed, operative position at the distal end of device 100. A deodorizing cartridge 70' is in position within the lumen of the catheter portion of the ostomy device and an anti-reflux valve is deflated to permit gasses to seep through the cartridge and out through the vent hole(s) in the closure member.

Figure 21B:
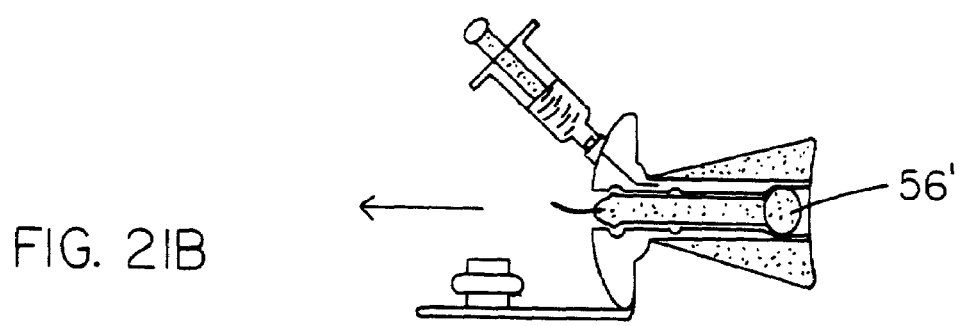

FIG. 21B shows device 100 with the closure member open, the cartridge partially backed out of the lumen until the anti-reflux valve is inflated by introduction of air with a conventional syringe via a schematically indicated one-way valve, such as a Halkey Roberts valve, into the minor lumen previously described. This step is reversed when it is time to reinsert a new cartridge.

Figure 21C:
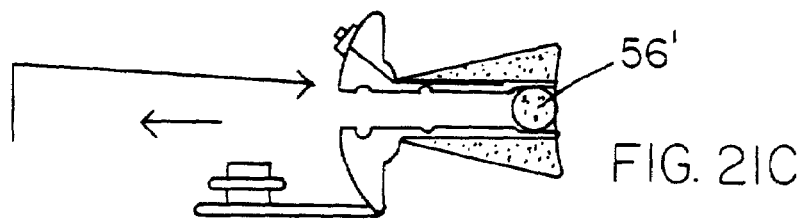
Figure 21D:
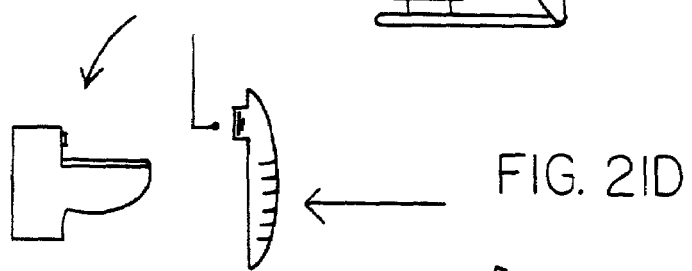

In the step illustrated at FIG. 21C an ostomy bag is connected to the open, distal end of device 100. Thereafter, the anti-reflux valve can be completely deflated to permit body waste to exit into the bag, or, more commonly, a drainage tube, such as that shown in FIG. 22, for example. Once the intestinal (or other stoma site organ) contents are voided the anti-reflux valve is again completely inflated and the entire bag and contents thereof are flushed away into a commode, as indicated in FIG. 21D.

Figure 21E:
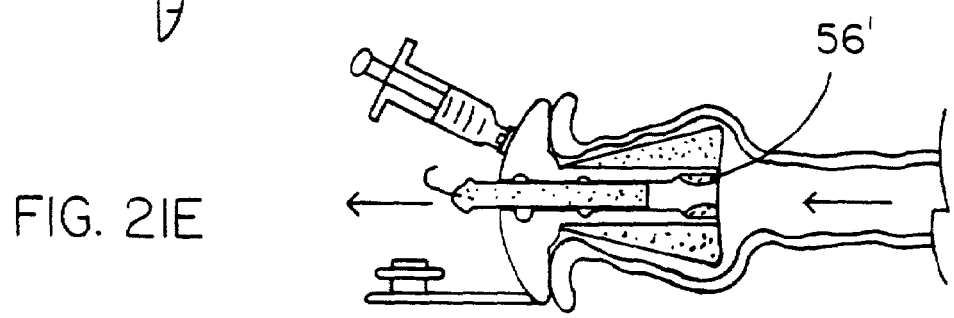

Finally, as shown in FIG. 21E, a fresh deodorizing cartridge is partially inserted and the anti-reflux valve is deflated. When the anti-reflux valve is completely deflated, the new cartridge is fully seated in the device 100 and the cap of the closure member is then closed (not shown in this view), permitting gasses to freely seep through the cartridge while maintaining liquid and solid body waste securely within the ostomy.

Figure 22:
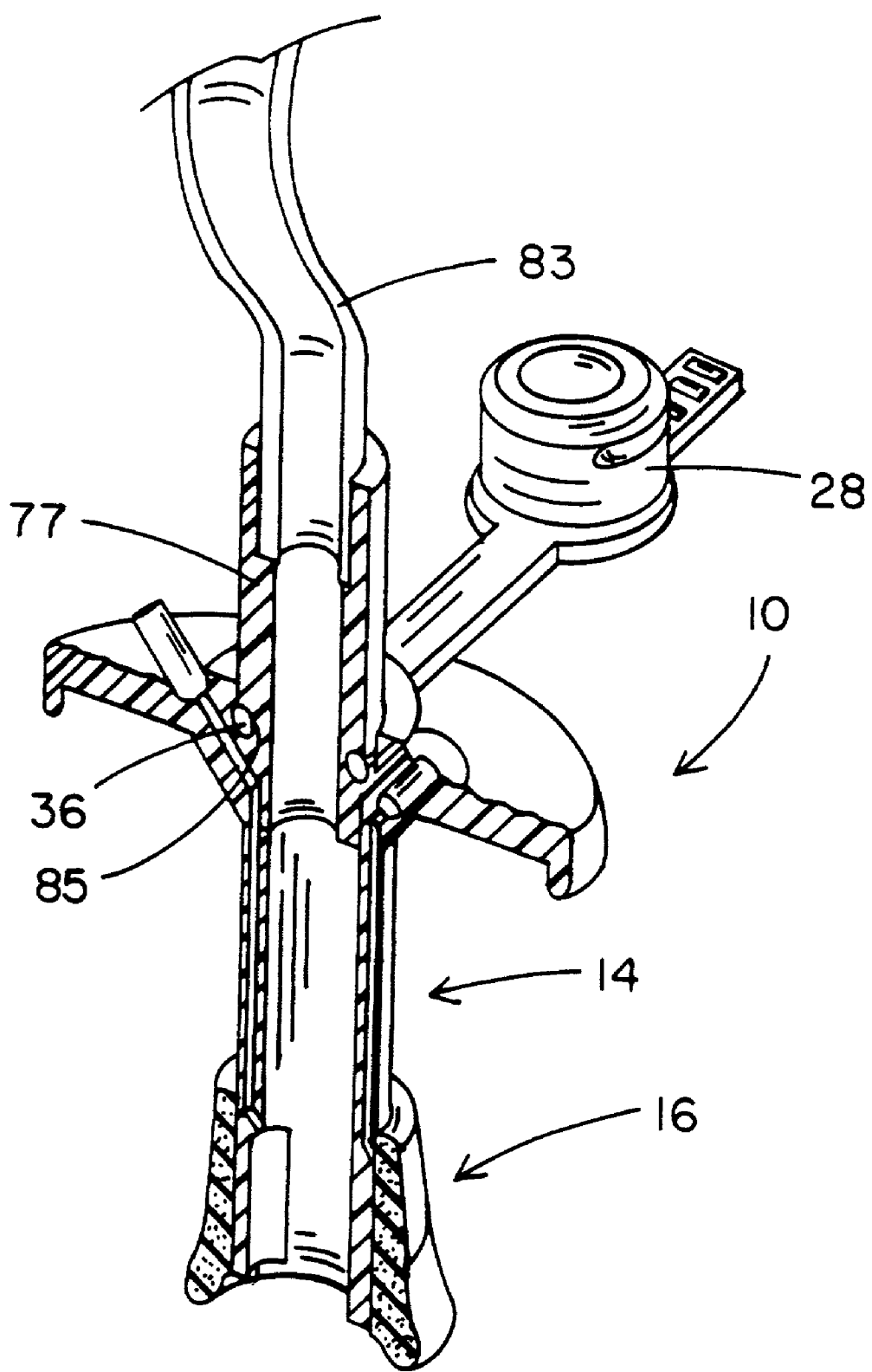
FIG. 22 is a schematic, longitudinal sectional view of the device of FIG. 1 with a standard drainage tube connected with a drain connector adapted for secure, hands-free attachment of the drainage tube to the COP.
Figure 23:
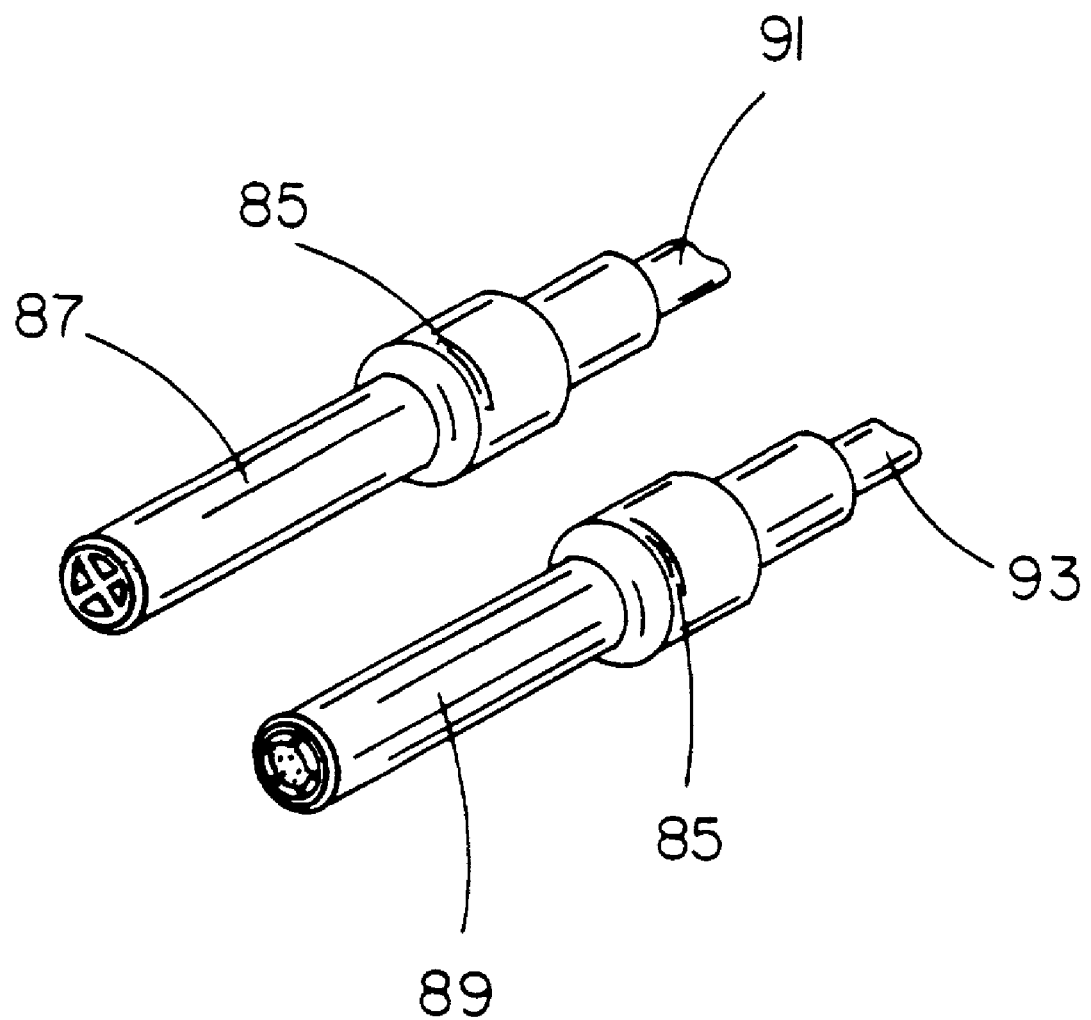
FIG. 23 is a partial perspective view of two examples of irrigation set connectors that can be used to connect to the new ostomy port and irrigate and cleanse the intestine.

FIGS. 22 and 23 illustrate a few types of accessories, which optionally may be used with the new ostomy port 10, 100 and useful variations of the embodiments thereof. It is to be understood that these devices are shown only as examples and do not limit the potential devices with which the new COP may be conveniently used.

FIG. 22 illustrates schematically, in longitudinal section, a connector 77 attached to one end of an ostomy drainage tube 83. Connector 77 is sized and shaped to provide a liquid-tight fit within collar 24 and to engage and lock onto detent bars 36, as by corresponding detenting grooves, similar to those described with regard to cap 28 and thus is designed particularly for the ostomate's selective and convenient use in combination with COP 10.

FIG. 23 shows two irrigation set connectors 87, 89 for attaching suitable tubing 91, 93 (preferably medical grade), respectively to irrigation and/or drainage sets to COP 10. Connectors 87, 89 are adapted for liquid-tight, interlocking connection within collar 34, and preferably include detent grooves 85 which function the same as those on closure portion 18 (element number 40), by engaging and retaining detent bars 36. With a connector 87, 89 so securely engaged within port 10 the user can proceed with the necessary hygienic processes "hands-free"; i.e., without the necessity of holding the drainage/irrigation tube connector in place at the port. Rather, the user's hands are available to do other things, such as shaving, for example, while the irrigation process takes place. Alternatively, for use with ostomy port device 100, the accessory connectors can be provided with a detenting annular ridge. This alternative structure and the hands-free use feature are also common to the just described drainage tube connector illustrated in FIG. 22.

FIGS. 24 through 26 schematically illustrate a further optional feature of COP 10, which can conceivably, although less conveniently, be adapted to COP 100, as well. FIG. 24 shows the distal portion of COP 10, without the cap, in longitudinal section. An annular ridge or pawl 45 protrudes slightly into lumen 26, just proximally of shoulder 35. Ridge 45 is palpably contacted by corresponding ridges on a variety of ostomy accessories. For example, ridges 47, 51 on an irrigation set connector 49 or a cone-tipped obturating device 53, respectively, such as those illustrated in FIGS. 25 and 26 will bump over ridge 45 as such devices are pushed into or pulled out of port 10. The purpose of this feature is to provide the user with sufficient additional resistance to tactilely detect that the accessory being removed is sufficiently far out of lumen 26 that the anti-reflux valve should be activated to prevent accidental release of body wastes.

Once the ARV is fully inflated the accessory in use can be completely removed from port 10 and cleaned or discarded. Useful alternatives to the above-described structure include replacement of pawl 45 with one or more slightly raised bumps or arcuate but non-annular ridges, so that less irregular surface area is present which can trap fecal material within lumen 26.

Figure 27:
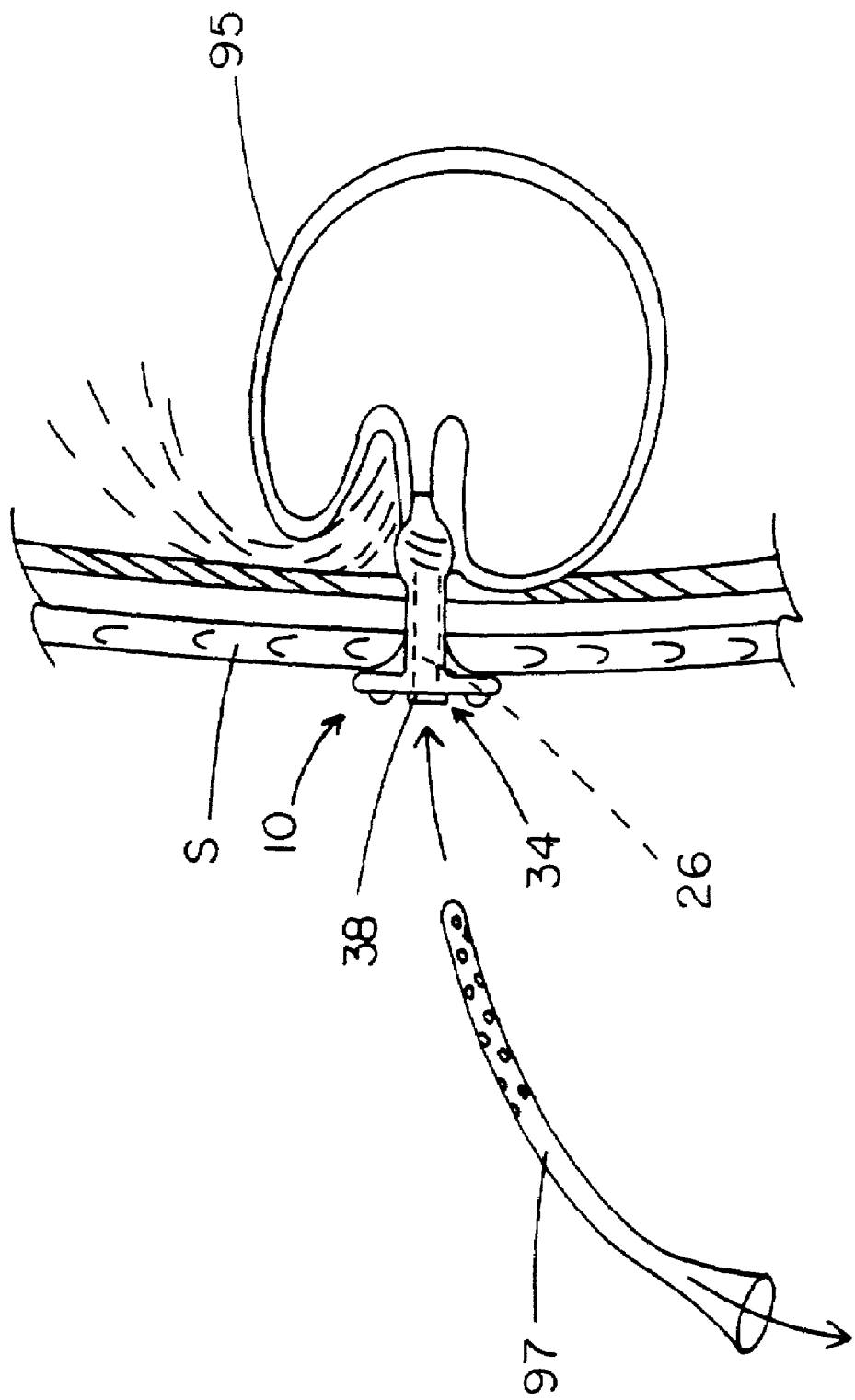
FIG. 27 is a sectional schematic view of the ostomy device of FIG. 1 in situ, connected to an internal collection reservoir and illustrating one type of drainage tube which can be used to selectively empty such a reservoir.

FIG. 27 schematically illustrates another practical use for ostomates having the new COP 10, 100 in operative position. For those ostomates who have a surgically created internal reservoir 95, such as the types commonly known as "Kock" and "Indiana" pouches, for waste collection. These patient's have historically been provided with a nipple valve formed of the patient's own tissue. Unfortunately these tissue valves are notorious for a high failure rate. Now, such nipple valves may not be necessary, and, as an alternative device 10 can be implanted through the skin, indicated in section at S, and the patient's abdominal wall such that catheter 24 provides external fluid communication from the reservoir 95 to exterior of the body.

In the case illustrated in FIG. 27, device 10 (or 100 and the corresponding structure thereof) can be kept with the cap closed and with the anti-reflux valve not activated until it is necessary to void the contents of the reservoir. Cap 38 is then opened and, with the cartridge partially retracted the ARV valve is fully activated, and then the filter cartridge (previously described, not shown in this view) is completely removed and a drainage tube 97 of known variety, such as that commonly known as the "Median-type tube", or any new or equivalent such tube, which will fit snugly into lumen 26, or sealingly into collar 34, is inserted. Then the anti-reflux valve is fully opened and the reservoir contents are voided into a toilet or other appropriate container (not shown).

Use of the new continent ostomy port and accessories thereto is very simple and can be managed by the ostomate or a caregiver with very little training. The user ostomate has the benefit of new port 10 as a barrier to withhold all bowel contents intestinally until drainage is desired. Although serving as a barrier to the internal bowel, new device 10 is primarily a continent port which allows passage of bowel gasses through the odor controlling filter cartridge and the vented cap to prevent painful buildup of bowel gas and bloating which would necessarily occur if no venting were provided. Then, when drainage of fecal (or other body waste) matter is desired, the ostomate engages the anti-reflux valve to temporarily seal the proximally disposed (internal) end of the lumen of the port.

The closed ARV valve thereby prevents any inadvertent escape of fecal material into the port while the odor control cartridge is being removed and a drainage or irrigation device is being attached (during ostomy drainage and/or colostomy irrigation). Then the ostomate removes, cleans and reinserts, or replaces the cartridge. Alternatively, a conventional, non-flushable bag can be temporarily connected to the port, if necessary. After the inflation/drainage process is complete, the ostomate cleans and reinserts or replaces the cartridge, depending upon the user's preference at the time.

Upon connection of the desired accessory, for example, as illustrated in FIG. 22, the user will simply deactivate the anti-reflux valve and purge the bowel of its contents. The purging process, as well as irrigation of the bowel can be done in the conventional manner, with the advantageous exception that once the irrigation or purging tube is connected the user's hands are free to attend to other tasks, such as shaving, make-up application, or otherwise, all while either the purging or irrigation process is carried on. Once drainage of the intestine is complete, and prior to removal of accessory from the COP aperture 24, the ARV is again activated while a new odor control cartridge is inserted. Then the anti-reflux valve is fully deactivated (opened) and the vented cap is returned to the closed position, permitting the ostomate to go on about the business of daily life. The ostomate is thus free of the burdens of cumbersome and uncomfortable bag attachments, constant concerns regarding unpleasant odors, noises, leakage and tissue irritations, and continual discomfort and expense associated with dependence on external bonding substrates such as glues, gums, and pastes or belts and straps.

With reference to FIGS. 28 through 35, there is disclosed another embodiment of the moisture barrier previously discussed herein with reference to FIG. 4. FIGS. 28–30 illustrate a "shim", generally designated 157, which is optionally used with a moisture barrier/pad 158 described hereafter. Shim 157 is substantially flat and in the preferred embodiment shown has a generally oval-shaped perimeter 157a, as illustrated in FIG. 28. Perimeter 157a is shaped to match the perimeter of pad 158. Thus, if the shape of the pad is something other than oval, if desired, the exterior perimeter of shim 157 can be altered accordingly. The overall size of shim 157 can vary, as desired, to either match the size of moisture barrier/pad 158, so as to act as a riser for the COP face plate, or the shim may be sufficiently smaller in exterior dimension to permit it to be seated within the underside (proximally) of COP 200 for enhanced absorption of stomal fluids.

The sectional views shown in FIGS. 29 and 30 illustrate an example of useful dimensions (in inches) for shim 157, but it is foreseen that other dimensions will suffice, depending upon the particular circumstances of use, including stoma size and COP dimensions.

Shim 157 has a preferably circular interior side wall, which defines a through-hole 157b to surround the stoma. The size and shape of the throughhole can be varied as may be necessary to accommodate any variations in size and shape stomas of various individual users. The arrow indicated by "X" in FIG. 29 illustrates one useful surface site on shim 157 for optional application of an adhesive, such as a pressure sensitive adhesive and/or web adhesive, for example.

FIGS. 31–35 illustrate an alternative embodiment, generally designated 158, of the new moisture barrier/pad. Inconsistencies in size between the figures may exist due to copying anomalies. In the preferred version shown, pad 158 is formed of molded foam material and has a low profile, as seen if FIG. 33, with a generally oval perimeter 158a (FIG. 35), although other perimeter designs can be useful. The pad body 159 has an outer (distal) surface 159a that is slightly domed, but formed in the central portion thereof with an indented region that accommodates the distal portions of a COP, such as that generally designated as 200 in FIG. 32. In this embodiment, upper surface 159a is formed with a central depressed area that is generally cross-shaped, extends down into the body 159 and has a substantially flat floor 163. Floor 163 defines a central aperture 160 with a side wall 161, which is shown circular, but can be other shapes, if desired, to accommodate the shape of a catheter, such as that indicated at 214 in FIG. 32.

Figure 31:
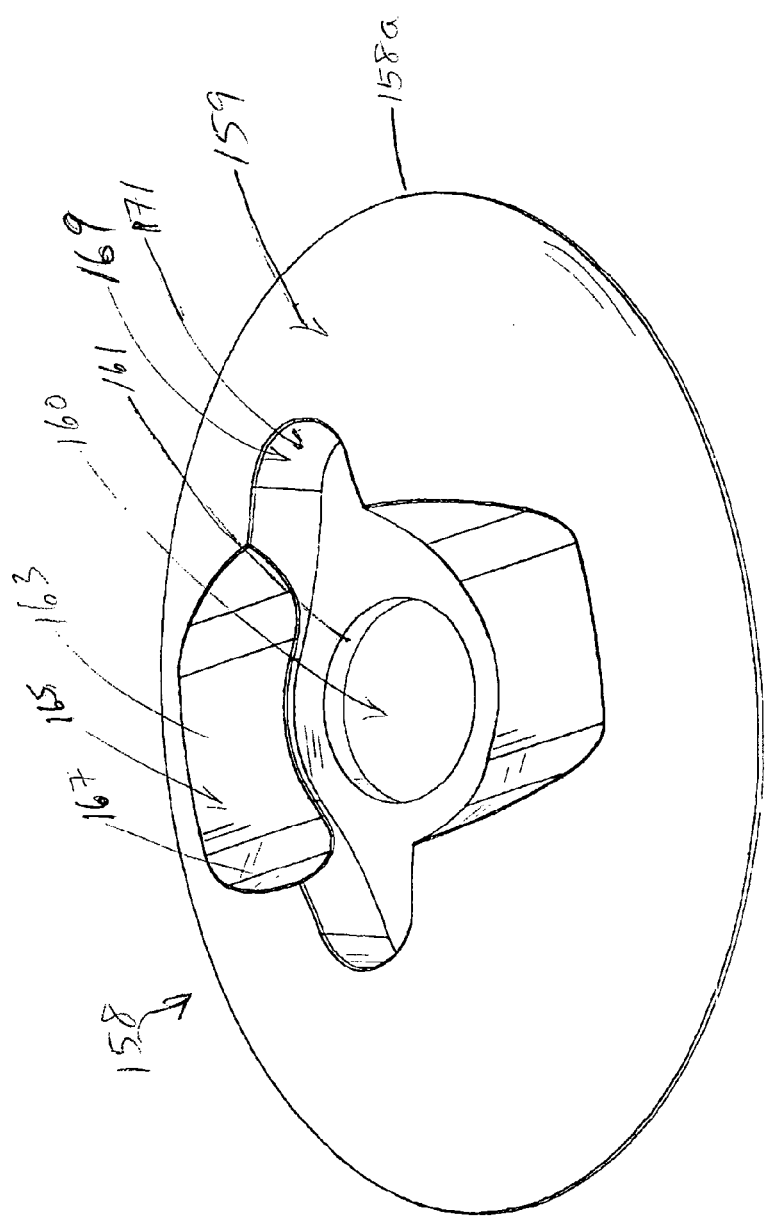
FIG. 31 is a schematic upper perspective view of another embodiment of a moisture barrier/pad constructed in accordance with the present invention.
Figure 32:
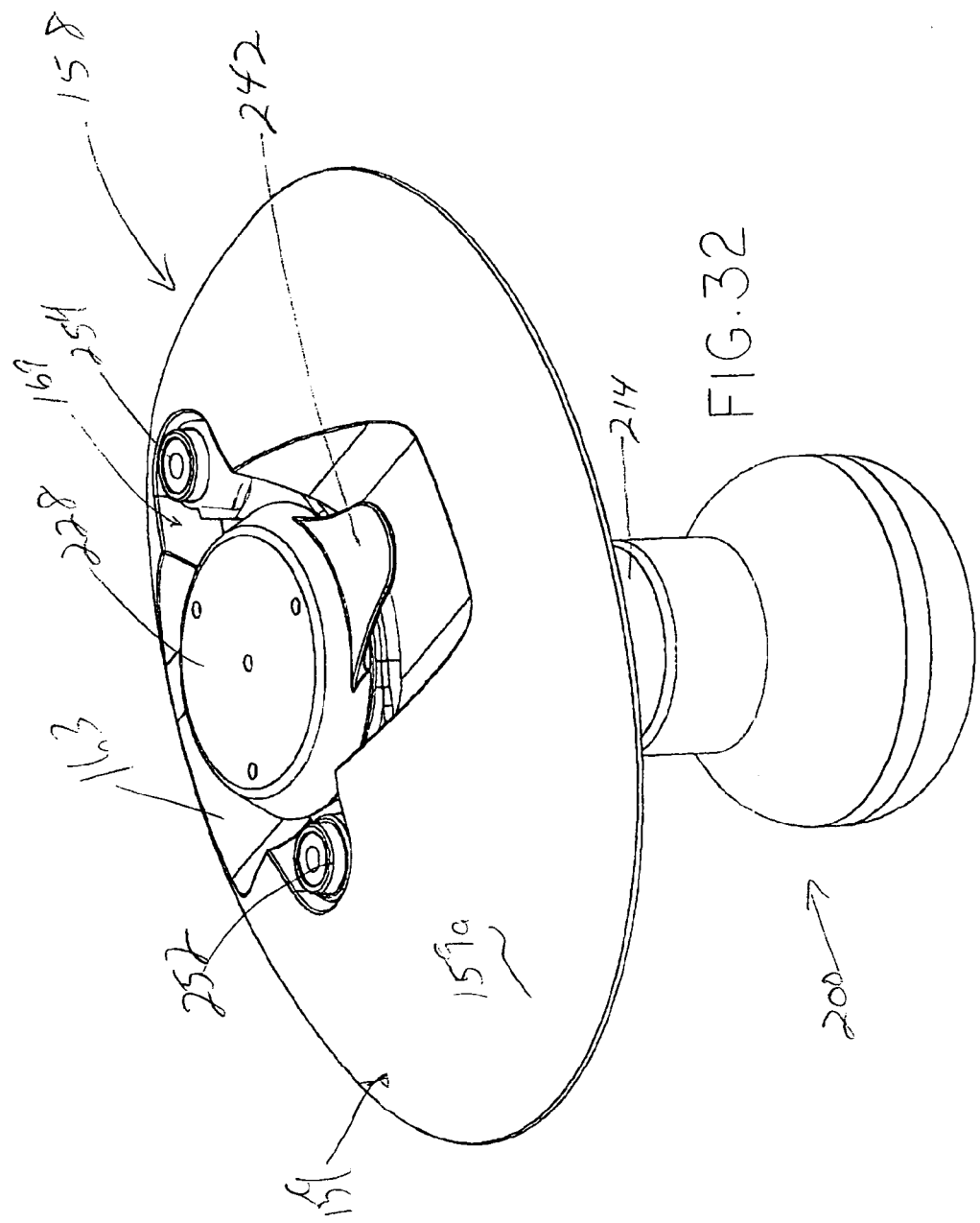
FIG. 32 is the same view as FIG. 31, but with a COP shown in place, to illustrate use of the pad.
Figure 33:
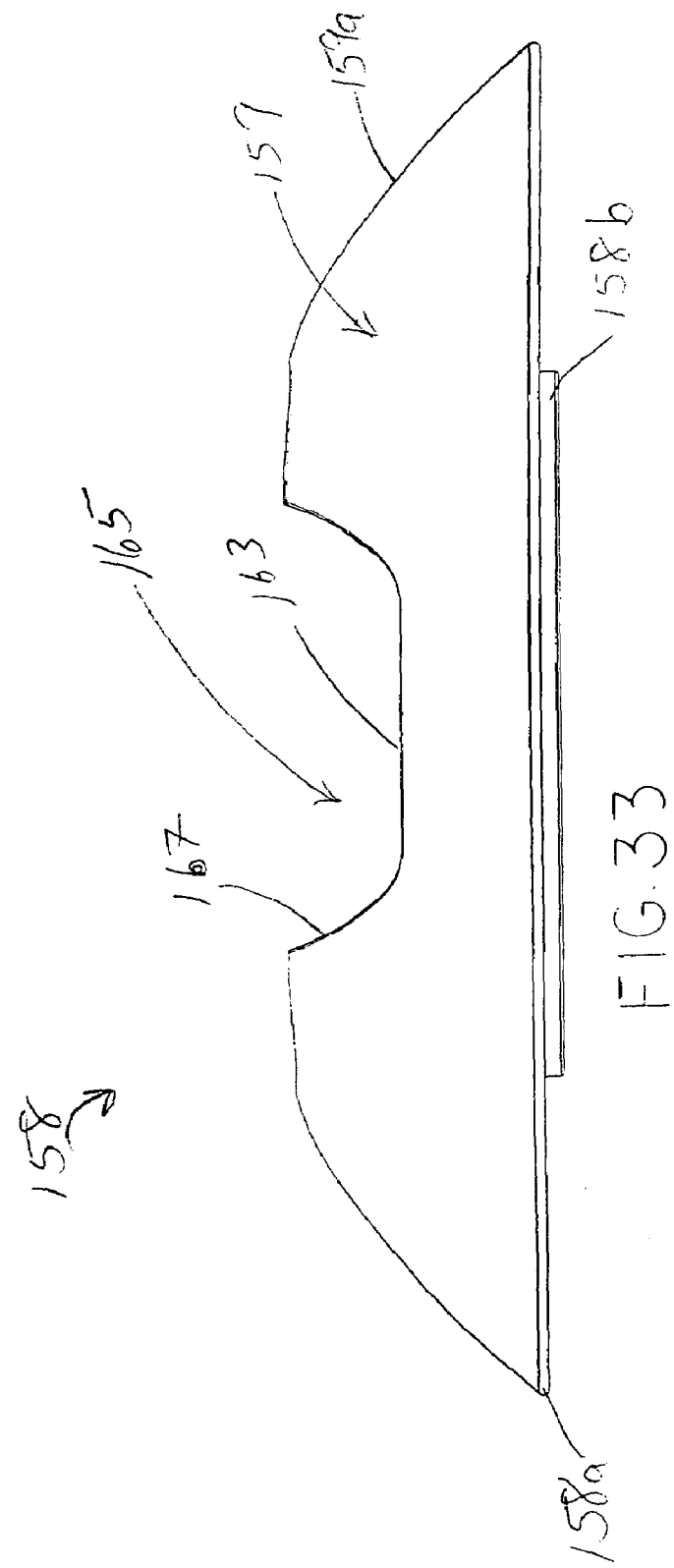
FIG. 33 is a side elevational view of the pad of FIG. 31.

Floor 163 of pad 158 extends away from aperture 160 in two opposed channels 165, each having opposed, angled side walls 167, as seen most clearly in FIGS. 31, 32 and 33. Channels 165 offer easy finger access to an optional grip 242 on a cap 228 of a COP.

Floor 163 extends at approximate right angles to channels 165 from aperture 160 in two opposed cut-out areas 169 bounded by arcuate walls 171 disposed radially outwardly from the center of pad 158. Floor 163 between cut-out areas 169 may be in the same plane as floor 163 between channels 165, if desired, or slightly stepped down, as is preferred and as is shown in FIG. 31. Cut-out areas 169 provide spaces in pad 158 to accommodate the COP 200 features, such as a bolster inflation port, as indicated at 252, or an access port for an ARV, as indicated at 254 in FIG. 32.

Figure 34:
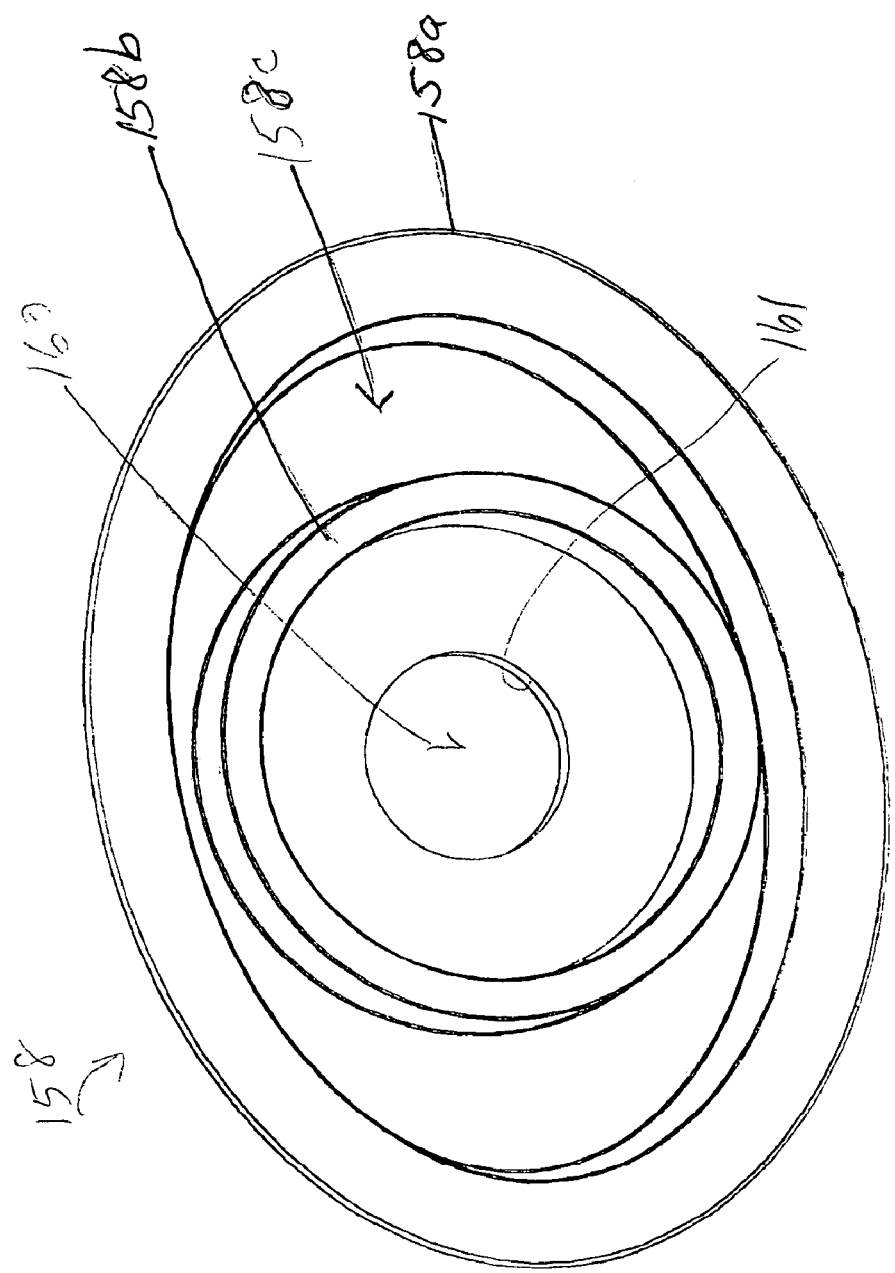
FIG. 34 is a bottom perspective view of the pad of FIG. 31.
Figure 35:
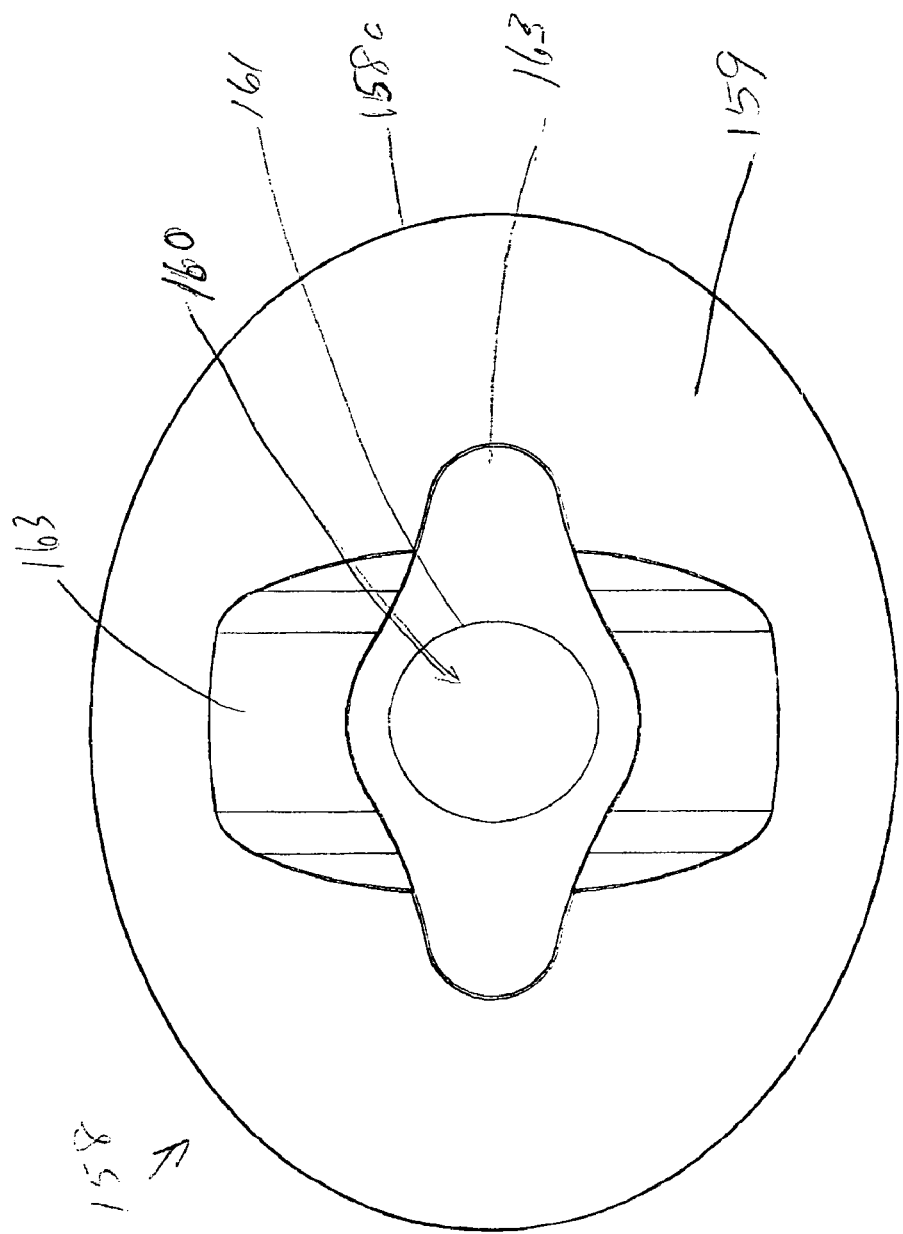
FIG. 35 is a top plan view of the pad of FIG. 31.

FIG. 34 shows that the lower (proximal) surface of pad 158 is preferably, although not necessarily, provided with a depending ring 158b. Ring 158b is disposed coaxially with opening 160, but spaced radially outward from opening 160 by a sufficient distance that ring 158b can be positioned outwardly of the stoma when pad 158 is in normal use position. Ring 158b preferably extends transverse to pad body 159, and slightly past the proximal extent of body 159, as illustrated in FIG. 33. Alternatively, ring 158b can be omitted altogether, or can be shorter than the depth of the perimeter of pad 158. When ring 158b is present, a preferably continuous channel 158c is formed between ring 158b and perimeter 158a of pad 158. Channel 158c is optionally sized and shaped to correspond to and to receive shim 157, so that shim 157 is disposed in normal use between the bottom of pad 158 and the user's skin. Shim 157 can also be nested in the underside of pad 158 without the presence of ring 158b. This arrangement is especially useful if the shim is to provide wicking properties. Alternatively, as previously discussed, the shim can have exterior dimensions which correspond to the exterior perimeter dimensions of pad 158, or which even extend slightly beyond the perimeter of the pad.

In view of the foregoing, it will be seen that the several objects of the invention are achieved and other advantages are attained.

Although the foregoing includes a description of the best mode contemplated for carrying out the invention, various modifications are conceivable.

As various modifications could be made in the constructions herein described and illustrated without departing from the scope of the invention it is intended that all matter contained in the foregoing description or shown in the accompanying drawings shall be interpreted as illustrative rather than limiting. For example, the overall shape and size of both the face plate and the catheter portions of port 10 can be varied.

What is claimed is:

1. A pad for use with a continent ostomy port, the pad comprising a body portion having an internal wall defining an aperture appropriately sized to place around a stoma, the body portion of the pad being sized and shaped for placement against a user's skin beneath a face plate of an ostomy port, the pad being formed of a soft, flexible material to thereby cushion and protect the skin from contact with the ostomy port face plate, wherein the body portion of the pad has a stepped configuration on a distal surface thereof, the stepped configuration consisting of at least two distinct levels; and wherein the at least two distinct levels comprise a first level and a second level, the first level having a perimeter sized and shaped appropriately to readily fit within a perimeter of a face plate lip of a continent ostomy port, and the second level extending parallel to the first level and having a perimeter extending beyond the perimeter of the first level, beneath the lip of the plate, to thereby protect the user's skin from friction irritation.

2. The pad of claim 1, wherein the pad is formed of a material which is readily disposable.

3. The pad of claim 1, wherein the pad is formed of a material that is capable of being facilely cleaned and reused.

4. The pad of claim 1, wherein the distal surface of the pad is coated with a thin, liquid impermeable skin to thereby trap wicked moisture within the pad.

5. The pad of claim 4, and further wherein the liquid impermeable skin is permeable to air, to thereby permit the pad area to breathe.

6. A pad for use with a continent ostomy port, the pad comprising a body portion defining an aperture appropriately sized to place around the catheter of a continent ostomy port, the body portion of the pad being sized and shaped for placement against a user's skin beneath a face plate of the ostomy port, the pad being formed of a soft, flexible material to thereby cushion and protect a user's skin from contact with the ostomy port face plate, wherein the pad body portion has a distal surface provided with a central indented region to thereby accommodate the distal portions of the continent ostomy port.

7. The pad of claim 6, wherein the central indented region of the distal surface of the pad body portion is generally cross-shaped.

8. The pad of claim 6, wherein the central indented region of the distal surface of the pad body portion has a substantially flat floor.

9. The pad of claim 6 wherein the central indented region of the distal surface of the pad body portion has a floor that defines the aperture for placement around a catheter of the continent ostomy port.

10. The pad of claim 6, wherein the distal surface of the pad is domed and the central indented region includes two opposed channels extending radially away from the center of the pad, to thereby permit access to a finger grip on a distal end of the continent ostomy port.

11. The pad of claim 6, wherein the central indented region includes two opposed cut-out areas extending radially away from the center of the pad, to thereby accommodate structural features on a distal end of the continent ostomy port.

12. The pad of claim 6, wherein the pad includes a proximal surface having a depending ring disposed coaxially with the aperture in the pad and spacedly outwardly therefrom.

13. The pad of claim 12, and further comprising a channel formed between the depending ring and the perimeter of the pad.

14. The pad of claim 12, and further comprising a layer of adhesive on the proximal surface of the pad.

15. The pad of claim 6, wherein the pad is formed of a disposable material.

16. The pad of claim 6, wherein the pad is formed of a material which can be cleaned and reused.

17. The pad of claim 6, wherein the body of the pad is generally oval.

18. The combination of a pad for use with a continent ostomy port and a shim, wherein the pad comprises a body portion defining an aperture appropriately sized to place around the catheter of a continent ostomy port, the body portion of the pad being sized and shaped for placement against a user's skin beneath a face plate of the ostomy port, the pad being formed of a soft, flexible material to thereby cushion and protect a user's skin from contact with the ostomy port face plate, wherein the pad body portion has a distal surface provided with a central indented region to thereby accommodate distal portions of the continent ostomy port, wherein the pad includes a proximal surface; and a shim having a through hole positioned coaxially with the aperture in the pad on the side of the proximal surface of the pad.

19. The combination of claim 18, wherein the pad has a depending ring on the proximal surface thereof, the depending ring being disposed coaxially with the aperture in the pad and spaced radially outwardly therefrom to thereby provide a channel between the depending ring and the perimeter of the pad and the shim has an overall size and shape to permit the shim to fit snugly within the channel formed in the proximal surface of the pad.

20. The combination of claim 18, wherein the shim has an overall size and shape sufficient to permit the shim to hold the pad away from the user's skin.

21. The combination of claim 18, and further comprising a layer of adhesive on the proximal surface of the pad.

22. The combination of claim 18, wherein the perimeter of the pad is substantially oval.

23. The combination of claim 18, wherein the body of the pad is generally domed.

24. The combination of claim 18, wherein the distal surface of the pad is coated with a thin, liquid impermeable skin to thereby trap wicked moisture within the pad.

25. The combination of claim 18, and further comprising a layer of adhesive on at least one of the distal side and the proximal side of the shim.

26. A method for protecting the skin of a user around a stoma of the user, comprising:

attaching a pad around a continent ostomy port, the pad having a body portion defining an aperture appropriately sized to place around a catheter of the continent ostomy port, and a distal surface provided with a central indented region to thereby accommodate distal portions of the continent ostomy port; and positioning the pad beneath a face plate of the ostomy port against the user's skin for cushioning and protecting the user's skin from contact with the ostomy face plate.

27. The method of claim 26, and further comprising the step of providing a shim having a through-hole and positioning the shim so that the through-hole aligns with the aperture in the pad.

28. The method of claim 27 wherein the pad includes a proximal surface having a depending ring disposed coaxially with the aperture in the pad and spacedly outwardly therefrom and a channel formed between the depending ring and the perimeter of the pad, and the method further comprises disposing the shim snugly within the channel formed in the proximal surface of the pad between the depending ring and the perimeter of the pad.

* * * * *

UNITED STATES PATENT AND TRADEMARK OFFICE
CERTIFICATE OF CORRECTION

PATENT NO. : 7,087,041 B2  Page 1 of 1
APPLICATION NO. : 09/995012
DATED : August 8, 2006
INVENTOR(S) : Peter M. von Dyck It is certified that error appears in the above-identified patent and that said Letters Patent is hereby corrected as shown below:

| Column No./Line No. | Reads | Should Read |
|---|---|---|
| Col. 22, Line 41 | "to thereby pennit" | -- to thereby permit -- |

Signed and Sealed this

Thirty-first Day of October, 2006

JON W. DUDAS
*Director of the United States Patent and Trademark Office*